US 8,864,737 B2

(12) United States Patent
Hasegawa et al.

(10) Patent No.: US 8,864,737 B2
(45) Date of Patent: Oct. 21, 2014

(54) DRUG SOLUTION PREPARING KIT

(75) Inventors: Mitsuru Hasegawa, Osaka (JP); Atsushi Ishikawa, Osaka (JP); Suguru Oyagi, Osaka (JP); Takeshi Ohguro, Osaka (JP)

(73) Assignee: Nipro Corporation, Osaka (JP)

( * ) Notice: Subject to any disclaimer, the term of this patent is extended or adjusted under 35 U.S.C. 154(b) by 458 days.

(21) Appl. No.: 13/414,501

(22) Filed: Mar. 7, 2012

(65) Prior Publication Data

US 2012/0172829 A1  Jul. 5, 2012

Related U.S. Application Data

(62) Division of application No. 12/305,640, filed as application No. PCT/JP2007/062355 on Jun. 19, 2007, now Pat. No. 8,211,082.

(30) Foreign Application Priority Data

Jun. 19, 2006  (JP) ................. 2006-168548
Jul. 27, 2006  (JP) ................. 2006-205203

(51) Int. Cl.
*A61M 5/32* (2006.01)
*A61J 1/20* (2006.01)
*A61M 5/162* (2006.01)
*A61J 1/10* (2006.01)
*A61J 1/14* (2006.01)

(52) U.S. Cl.
CPC . *A61J 1/2096* (2013.01); *A61J 1/10* (2013.01); *A61J 1/1475* (2013.01); *A61J 2001/2013* (2013.01); *A61J 2001/2072* (2013.01); *A61M 5/162* (2013.01); *A61M 2005/1623* (2013.01); *A61M 2205/7536* (2013.01); *A61J 2001/2086* (2013.01); *A61J 2001/2017* (2013.01); *A61J 2001/2058* (2013.01); *A61J 2001/2062* (2013.01); *A61J 2001/2075* (2013.01)
USPC ........... 604/416; 604/411; 604/412; 604/413; 604/414; 604/415

(58) Field of Classification Search
CPC ................. A61J 2001/2017; A61J 2001/2068; A61J 1/2096; A61M 5/162
USPC ................................................ 604/411–416
See application file for complete search history.

(56) References Cited

U.S. PATENT DOCUMENTS

| 4,927,423 A | 5/1990 | Malmborg |
| 5,049,129 A | 9/1991 | Zdeb et al. |
| 5,445,630 A | 8/1995 | Richmond |
| 5,478,337 A | 12/1995 | Okamoto et al. |

(Continued)

FOREIGN PATENT DOCUMENTS

| DE | 41 22 476 A1 | 1/1993 |
| EP | 1 498 097 A2 | 1/2005 |

(Continued)

*Primary Examiner* — Leslie Deak
(74) *Attorney, Agent, or Firm* — Birch, Stewart, Kolasch & Birch, LLP

(57) ABSTRACT

To provide a drug solution preparing kit which can be handled with ease in a substantially aseptic manner, and has no risk that a leakage of a drug solution such as a splash and a dispersion of an aerosol to an ambient environment occurs upon preparation of the drug solution There is provided a drug solution preparing kit including a pre-filled syringe and a transfusing tool, wherein the pre-filled syringe includes a sealing member which seals the tip end and can not be removed from the tip end, and that the transfusing tool includes a one-way valve which can discharge only gas from the system in an irreversible manner, and a filter which is provided so as to adjoin to the second communication channel with respect to the one-way valve.

9 Claims, 16 Drawing Sheets

(56) References Cited

U.S. PATENT DOCUMENTS

| | | |
|---|---|---|
| 2001/0029360 A1 | 10/2001 | Miyoshi et al. |
| 2003/0191445 A1 | 10/2003 | Wallen et al. |

FOREIGN PATENT DOCUMENTS

| | | |
|---|---|---|
| JP | 49-3187 Y | 1/1974 |
| JP | 50-13428 Y1 | 4/1975 |
| JP | 53-30152 Y | 7/1978 |
| JP | 7-8555 A | 1/1995 |
| JP | 7-59865 A | 3/1995 |
| JP | 2001-286534 A | 10/2001 |
| JP | 2001-286561 A | 10/2001 |
| JP | 2001-321416 A | 11/2001 |
| JP | 2005-522281 A | 7/2005 |
| JP | 2006-116223 A | 5/2006 |
| WO | WO 97/46203 A1 | 12/1997 |
| WO | WO 03/086529 A1 | 10/2003 |
| WO | WO 2006/088783 A2 | 8/2006 |

DRUG SOLUTION PREPARING KIT

This application is a Divisional of application Ser. No. 12/305,640 filed on Jun. 5, 2009 now U.S. Pat. No. 8,211,082, which is the national phase of PCT International Application No. PCT/JP2007/062355 filed on Jun. 19, 2007, and which claims priority to Application No. 2006-168548 filed in the Japan on Jun. 19, 2006 and Application No. 2006-205203 filed in Japan on Jul. 27, 2006. The entire contents of all of the above applications are hereby incorporated by reference.

TECHNICAL FIELD

The present invention relates to a drug solution preparing kit.

BACKGROUND ART

In a medical institution such as a hospital, conventionally, a dry preparation such as a powdery drug or a freeze-dried drug, which is held in a drug container such as a vial, is used while being dissolved in a solvent or the like in an injection syringe. The resultant drug solution is used as an infusion for drip injection. Such a drug loses its efficacy in a state of a drug solution and, consequently, can not be stored in the state of the drug solution.

However, the mixing of the drug into the solvent by means of the injection syringe is a complicated process that requires time and effort, and has the following problem. That is, there is a possibility that the drug held in the vial is contaminated.

It is considered herein that a drug to be used for drip injection has a toxic property. In a case of a dried state, the toxic drug, which is held in a container such as a vial, is used in a form of a drug solution prepared by means of an injection syringe or the like and then is coinfused in an infusion container. In a case of a liquid state, on the other hand, the toxic drug is directly sucked into and collected by the injection syringe and then is coinfused in the infusion container. However, the coinfusion using the injection syringe is a complicated process that requires time and effort. Upon preparation of the toxic drug, moreover, in a state that a pressure is applied to a connection portion of the injection syringe irrespective of a level thereof or in a state that a hydraulic pressure in the infusion container is applied to the connection portion of the injection syringe, removal of the injection syringe causes a possibility that a splash or spill or the drug solution occurs at the connection portion. In the occurrence of splash or spill or after drying of the splashed or spilled solution, an aerosol generates and floats in the air. Such an aerosol is exposed in an ambient environment for a long period of time and causes the following problem. That is, there is a possibility that the aerosol exerts an adverse influence on health of medical staffs and patients.

In order to solve this problem, Japanese Patent Laying-Open No. 7-8555 proposes a pre-filled syringe. This pre-filled syringe includes a barrel filled with a solvent, a cylindrical communication supporting tool attached to an outer wall of a tip end of the barrel, and a communication means supported by the communication supporting tool. Herein, a vial attaching part is provided on the communication supporting tool and a communication means supporting part is provided below the communication supporting tool.

As an example of a tool for coinfusion in the infusion container, Utility Model Publication No. 49-3187 or Utility Model Publication No. 53-30152 proposes a solution collecting device. This device includes: a needle main body of a solution collecting needle, having a drug solution communicating inner cavity formed at a center in a longitudinal direction and an air and drug solution infusing groove formed at a sidewall in the longitudinal direction; a covering body having a branched tube protruding from a lower side thereof so as to be communicatively connected to the air and drug solution infusing groove, the covering body being used for covering the needle main body; and a cylinder body formed into a spherical shape or a shape similar thereto using a flexible material such as rubber or soft plastic in order to allow the air and the drug solution to pass only in an infusing direction, the cylinder body being provided with a check valve including a hollow valve part having a slit formed at a front side thereof and a hollow conduit part made of a material similar to that of the valve part and integrated with the valve part, the cylinder body being suitably fit into the branched tube.

It is considered that a toxic drug is used in this device. In such a case, first, a drug solution is introduced into an infusion container and is diluted without fail in the infusion container. Therefore, there is no possibility that the drug solution is administered in a high toxic state as a concentrate. Moreover, this device allows prevention of backflow of the drug solution to be coinfused and, therefore, allows suppression of a risk that the toxic drug is exposed in an ambient environment from a connection portion of an injection syringe. In addition, this device brings about an advantage that no injection needle is required.

However, the solution collecting device still has a possibility that the drug solution existing in a space formed between the check valve and a nozzle of the injection syringe is spilled upon removal of the injection syringe. Further, the integrated drip barrel hinders free selection of an infusion set, which causes increase in cost of the solution collecting device in some instances. Even when the space formed between the check valve and the nozzle of the injection syringe is made small as much as possible, there is a possibility that the liquid solution is drawn from the nozzle of the injection syringe and a spill of the drug solution occurs due to the following reason. That is, at an instant that the nozzle of the injection syringe is removed, the space is in a low pressure state temporarily.

In order to solve the problems of the solution collecting device described above, National Patent Publication No. 2005-522281 discloses the following device. That is, this device includes an inlet port which receives a first medical fluid, an infusion port through which a second medical fluid is infused, an outlet port which serves as an outlet of a mixed flow of the first and second medical fluids, a first duct which extends between the infusion port and the inlet port, and a second duct which extends between the inlet port and the outlet port. Herein, when the second medical fluid is infused, the infusion port is sealed with a fluid impermeable film through which an injection needle can penetrate. Thus, this device includes at least a first portion made of a first material and a second portion made of a second material. Herein, the second material is substantially higher in elasticity than the first material. The first portion includes the inlet port and the infusion portion, and the second portion includes the outlet port. The first and second portions are attached to each other by complex friction coupling and snap connection offering a first retention force.

According to this device, a toxic drug is infused only when the injection needle penetrates through the fluid impermeable film of the infusion port. Therefore, the toxic drug can be safely administered by drip without being exposed in the outside air. In a case where a fluid transferring device is attached to the nozzle of the injection syringe, particularly, a film is also attached to a tip end of the fluid transferring device. Therefore, safety is secured after cancellation of the connection because an outer face of the needle is not exposed to the outside.

Patent Document 1: Japanese Patent Laying-Open No. 7-8555
Patent Document 2: Utility Model Publication No. 49-3187
Patent Document 3: Utility Model Publication No. 53-30152
Patent Document 4: National Patent Publication No. 2005-522281

DISCLOSURE OF THE INVENTION

Problems to be Solved by the Invention

A toxic drug such as an anti-cancer drug is, when being released to an ambient environment upon preparation of a drug solution, poses a danger of expression of genetic toxic action, carcinogenicity, teratogenesis, serious tissue disorder and the like, and exerts an adverse influence on health of medical staffs and patients. Upon handling of the toxic drug, hence, the medical staffs use a protective mask, a protective glove, protective wear, a spill kit and the like in order to prevent direct exposure to the toxic drug in form of an aerosol or a splash and indirect exposure to the toxic drug from a peripheral adhesion factor.

However, a part of the aerosol floats for a long period of time, is dried when floating, and is turned into a small particle in a state that a drug concentration is high. Consequently, the medical staffs and the patients are exposed to the toxic drug even after the temporal protection is cancelled. The aerosol generates in a case where a solvent is directly jetted onto the drug when being introduced into a vial. Alternatively, the aerosol generates in a splash from a connection portion in a case where a pre-filled syringe is removed with an interior of a vial being pressurized. In particular, caution must be taken in the latter case. Upon preparation of the toxic drug, therefore, the pre-filled syringe must be removed in a state that at least the pressure in the vial is not increased.

In cited document 1, however, there is a possibility that the pressure in the vial is increased upon removal of the pre-filled syringe. Further, there is a possibility that the spill of the drawn toxic drug may occur because a pressure in an inner cavity of the connection portion is reduced instantaneously. Consequently, the pre-filled syringe still has a problem in order to avoid the risk of exposure to the toxic drug.

As described in cited document 4, the fluid transferring device or the injection needle to be connected to the fluid impermeable film must be connected to the open nozzle of the injection syringe, so that a combination thereof becomes large in size. In the case where an injection syringe to be used herein is the pre-filled syringe which is filled with the toxic drug in advance, there is a risk of exposure due to the leakage of the drug solution from the open nozzle upon connection to the fluid transferring device or the injection needle.

With regard to many toxic drugs which are not used for intravenous injection (i.e., which are used for coinfusion or drip administration), there are unpreferable cases, that is, a case where a normal injection needle can always be connected to the nozzle of the pre-filled syringe after completion of the preparation and a case where the nozzle of the pre-filled syringe is open such that the leakage of the drug solution occurs unintentionally.

The present invention has been devised in view of the circumstances described above, and an object of the present invention is to provide a drug solution preparing kit which can be handled with ease in a substantially aseptic manner, and has no risk that a leakage of a drug solution such as a splash and a dispersion of an aerosol to an ambient environment occurs upon preparation of the drug solution. Another object of the present invention is to provide a drug solution-filled syringe which can prevent intravenous administration of only a toxic drug before preparation of a drug solution and can also prevent erroneous connection.

Means for Solving the Problems

In order to achieve the object described above, the present inventors propose the following embodiments as a preparing kit for a vial.

That is, the present inventors propose a drug solution preparing kit including a pre-filled syringe and a transfusing tool, wherein the pre-filled syringe includes a cylinder-shaped barrel of which a tip end and a base end are open, a sealing member which seals the tip end and can not be removed from the tip end, and a plunger which is inserted into the barrel in a liquid-tight manner and a slidable manner, the barrel, the plunger and the sealing member define a space filled with a drug solution, the transfusing tool includes a barrel attaching part to which the tip end of the barrel is attached, a first needle which is provided on the barrel attaching part and can penetrate through the sealing member, a vial attaching part to which an inlet of a vial can be attached, a second needle which is provided on the vial attaching part and can penetrate through the inlet of the vial, a first communication channel which establishes communicative connection between the first needle and the second needle, and a second communication channel which establishes communicative connection between the second needle and a port and is formed independently of the first communication channel, and the port includes a one-way valve which can discharge only gas from the system in an irreversible manner, and a filter which is provided so as to adjoin to the second communication channel with respect to the one-way valve.

The present inventors also propose a drug solution preparing kit including a pre-filled syringe and a transfusing tool, wherein the pre-filled syringe includes a cylinder-shaped barrel of which a tip end and a base end are open, a sealing member which seals the tip end and can not be removed from the tip end, and a plunger which is inserted into the barrel in a liquid-tight manner and a slidable manner, the barrel, the plunger and the sealing member define a space filled with a drug solution, the transfusing tool includes a barrel attaching part to which the tip end of the barrel is attached, a first needle which is provided on the barrel attaching part and can penetrate through the sealing member, a vial attaching part to which an inlet of a vial can be attached, second and third needles which are provided on the vial attaching part and can penetrate through the inlet of the vial, a first communication channel which establishes communicative connection between the first needle and the second needle, and a second communication channel which establishes communicative connection between the third needle and a port, and the port includes a one-way valve which can discharge only gas from the system in an irreversible manner, and a filter which is provided so as to adjoin to the second communication channel with respect to the one-way valve.

In the drug solution preparing kit described above, the port includes a chamber which is connected to a side opposite to the second communication channel in a fluid-tight manner so as to adjoin to the one-way valve and receives the gas discharged from the system.

In the drug solution preparing kit described above, the first needle is covered so as to be communicatively connected only when the tip end of the barrel is attached to the barrel attaching part.

In the drug solution preparing kit described above, the first communication channel has an opening which is provided so as to prevent a liquid introduced from the barrel from being directly jetted to a bottom side of the vial.

In the drug solution preparing kit described above, the filter has a hydrophobic property.

In the drug solution preparing kit described above, the inlet of the vial can not be removed from the vial attaching part once being attached to the vial attaching part.

In the drug solution preparing kit described above, the first needle and the second needle are integrated into one.

With the use of the drug solution preparing kit described above, operations to be performed by a user are only to attach the barrel to the barrel attaching part, to attach the vial to the vial attaching part and to push/pull the plunger. Therefore, the present inventors has found the following advantages. That is, a drug can be readily prepared in an aseptic manner. Upon preparation of the drug, when the plunger is pushed, gas corresponding to an amount of a reduced volume is discharged from the system in an irreversible manner. After the preparation, therefore, even when the prepared drug is drawn into the barrel and the barrel is separated from the transfusing tool, the sealing member provided at the opening, which is the tip end of the barrel, blocks the barrel to prevent the leakage of the prepared drug. Moreover, when the prepared drug solution is drawn into the barrel, the pressure in the system is lower than that in an ambient environment. Even in a case where a splash occurs or an aerosol generates, therefore, the splash or the aerosol is caused inside the vial and the prepared drug solution is not dispersed outside the system. Thus, the present inventors have led the invention of this application.

The present inventor also proposes a drug solution preparing kit for an infusion container, that is, a drug solution preparing kit including a drug solution-filled syringe and a transfusing tool, wherein the drug solution-filled syringe includes a cylinder-shaped barrel of which a tip end and a base end are open, a sealing member which seals the tip end and can not be removed from the tip end, and a plunger which is inserted into the barrel in a liquid-tight manner and a slidable manner, the barrel, the plunger and the sealing member define a space filled with a drug solution, and the transfusing tool includes a barrel attaching part to which the barrel can be attached, a first needle which is provided on the barrel attaching part and can penetrate through the sealing member, a second needle which can penetrate through a plug body of an infusion container, an outlet port which is blocked with a blocking member through which a bottle needle of an infusion line can penetrate, a first communication channel which establishes communicative connection between the first needle and the second needle, a second communication channel which establishes communicative connection between the second needle and the outlet port and is formed independently of the first communication channel, a covering member which covers the first needle such that the first communication channel is open only when the barrel is attached to the barrel attaching part, and a one-way valve which is provided on the first communication channel and allows only a fluid flowing from a direction of a tip end of the first needle to pass therethrough in an irreversible manner.

In the drug solution preparing kit described above, an opening of the first communication channel, which is formed in the second needle, is farther in position than an opening of the second communication channel.

The present inventor also proposes a drug solution preparing kit including a drug solution-filled syringe and a transfusing tool, wherein the drug solution-filled syringe includes a cylinder-shaped barrel of which a tip end and a base end are open, a sealing member which seals the tip end and can not be removed from the tip end, and a plunger which is inserted into the barrel in a liquid-tight manner and a slidable manner, the barrel, the plunger and the sealing member define a space filled with a drug solution, and the transfusing tool includes a barrel attaching part to which the barrel can be attached, a first needle which is provided on the barrel attaching part and can penetrate through the sealing member, second and third needles which can penetrate through a plug body of an infusion container and are fastened to a fastening device such that axes thereof are directed in a single direction, an outlet port which is blocked with a blocking member through which a bottle needle of an infusion line can penetrate, a first communication channel which establishes communicative connection between the first needle and the second needle, a second communication channel which establishes communicative connection between the third needle and the outlet port, a covering member which covers the first needle such that the first communication channel is open only when the barrel is attached to the barrel attaching part, and a one-way valve which is provided on the first communication channel and allows only a fluid flowing from a direction of a tip end of the first needle to pass therethrough in an irreversible manner.

In the drug solution preparing kit described above, an opening of the first communication channel, which is formed in the second needle, is farther in position than an opening of the second communication channel which is formed in the third needle.

In the drug solution preparing kit described above, the second communication channel is provided with a stopcock.

In the drug solution preparing kit described above, the second communication channel is provided with a branched part, and a discharge port, which has a one-way valve allowing only gas from the system to pass therethrough and a hydrophobic filter, is provided so as to be communicatively connected to the branched part.

In the drug solution preparing kit described above, the branched part is provided with a stopcock capable of switching between the communicative connection from the second communication channel to the outlet port and the communicative connection from the second communication channel to the discharge port.

In the drug solution preparing kit described above, the opening of the first communication channel of the second needle is provided at a side portion of the second needle.

In the drug solution preparing kit described above, the coupling between the transfusing tool and the infusion container can not be cancelled once the second needle penetrates through the plug body of the infusion container.

In the drug solution preparing kit described above, the barrel attaching part includes a lock means for locking the barrel when the barrel is attached to the barrel attaching part, and the lock can be cancelled upon removal of the barrel from the barrel attaching part.

With the use of the drug solution preparing kit described above, the barrel into which a toxic drug is stored in advance is sealed with the sealing member. Therefore, there is no possibility of leakage of a drug solution. Further, there is no possibility that the barrel is used while being erroneously connected to a common needle and the like. In a case where the toxic drug is transfused from the barrel to the drug container, such a process can be performed in the closed system. In a case where the barrel is removed from the barrel attaching part, the check valve provided on the first communication channel prevents backflow of the prepared drug solution from the drug container. Moreover, the sealing member is open at the tip end of the barrel and the first needle is covered with the covering member, so that there is no possibility that the toxic drug remaining in the barrel or the first needle is leaked externally. Further, the high pressure in the drug container, to which the toxic drug has been transfused, can be released appropriately without the disadvantage that the prepared drug is leaked externally.

Further, the sealing member has a tip end on which an annular hood is formed. When a length of the annular hood formed at the tip end of the sealing member is long, the sealing member can be firmly attached to the barrel attaching part.

Effects of the Invention

The drug solution preparing kit according to the present invention can be readily handled in the aseptic manner. The port is provided with the one-way valve which can discharge only the gas from the system in the irreversible manner. Upon preparation of a drug, therefore, when the plunger is pushed, the gas corresponding to the amount of the reduced volume in the system is discharged from the system. Then, when the prepared drug solution is drawn into the plunger, the pressure in the system is reduced. As a result, there is no possibility that a splash of the hazard drug or an aerosol is jetted outside the system. Moreover, the tip end of the pre-filled syringe, in which the prepared drug is stored, is sealed with the sealing member, which can not be removed from the pre-filled syringe, in the liquid-tight manner. As a result, there is no possibility that the drug solution is leaked from the barrel. Hence, the drug solution preparing kit according to the present invention is safe because a toxic drug is not exposed in an ambient environment upon preparation of a drug solution and, therefore, can be used suitably upon preparation of a drug solution.

Moreover, the drug solution preparing kit according to the present invention can also bring about the following advantages. Since the operations to be performed by a user are only to connect the infusion container and the drug solution-filled syringe to the transfusing tool and to push the plunger. Therefore, the user can readily handle the drug solution preparing kit in the aseptic manner. Moreover, the barrel attaching part is provided with the one-way valve which can infuse the toxic drug in the syringe in the irreversible manner, and the covering member which covers the first needle such that the first communication channel is open only when the barrel is attached to the barrel attaching part. Upon preparation of a drug, therefore, even when the drug solution-filled syringe is removed from the transfusing tool, the drug solution preparing kit is safe because no splash or leakage of the toxic drug occurs and no aerosol is exposed in the ambient environment. Moreover, the drug solution preparing kit is not used solely in intravenous injection if necessary. Therefore, the drug solution preparing kit is safe because there is no possibility of erroneous connection.

DESCRIPTION OF THE REFERENCE SIGNS

Figure 1:
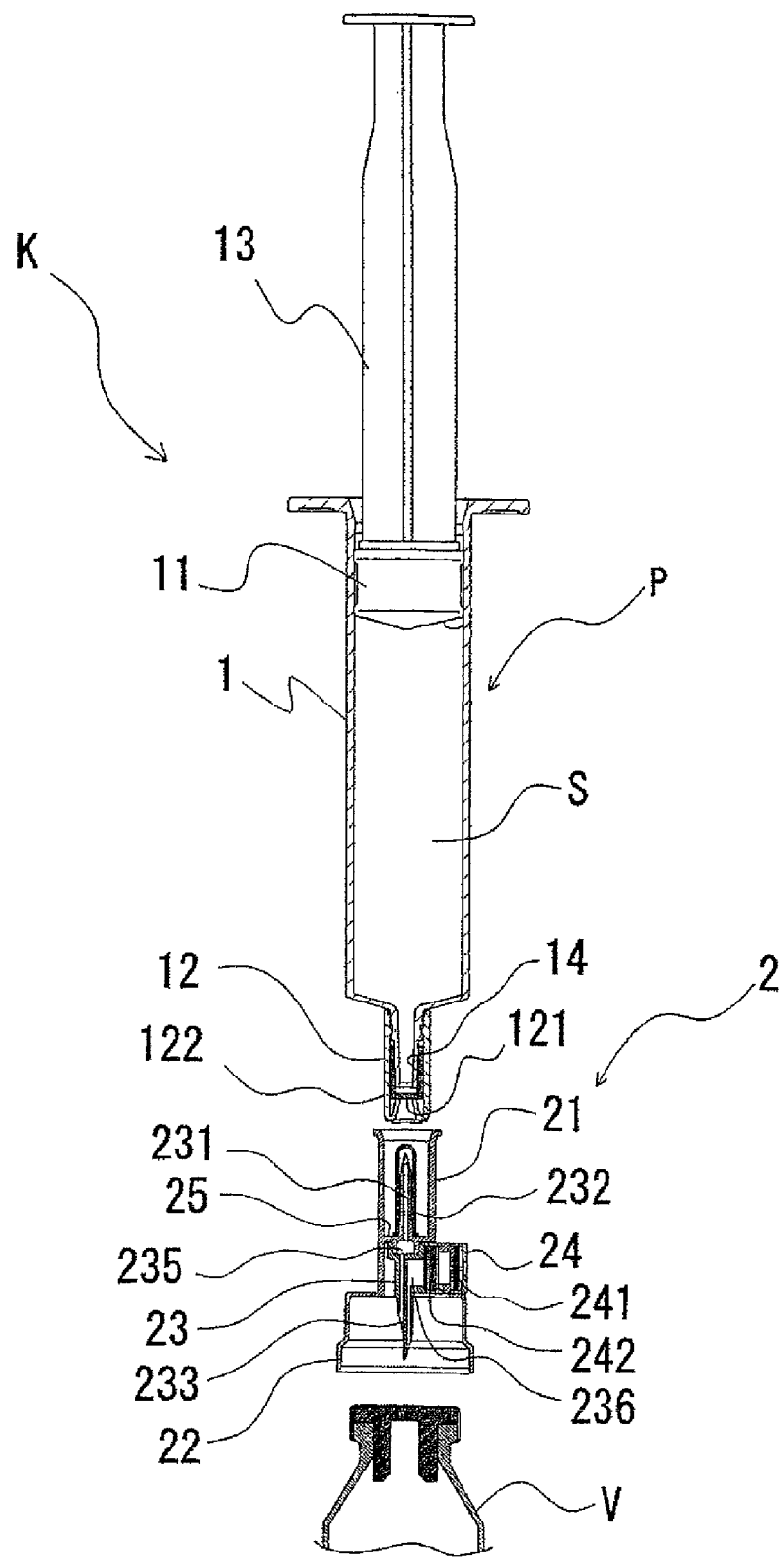
FIG. 1 is a vertical sectional view showing one embodiment example of a drug solution preparing kit according to the present invention which is used for a vial.

1: Barrel
11: Gasket
12: Sealing member
121: Elastic body film
122: Caulking member
13: Plunger
14: Nozzle
15: Hood
2: Transfusing tool
21: Barrel attaching part
22: Vial attaching part
23: Double ended needle
231: First needle
232: Covering member
233: Second needle
234: Third needle
235: First communication channel
236: Second communication channel
24: Port
241: One-way valve
242: Hydrophobic filter
243: Chamber 25: Partition wall
3: Transfusing tool
31: Barrel attaching part
32: First needle
321: Covering member
322: One-way valve
33: Second needle
331: Third needle
333: First communication channel
334: Second communication channel
34: Flange
35: Outlet port
351: Blocking member
352: Branched part
353: Stopcock
354: Discharge port
355: Hydrophobic filter
356: One-way valve for discharge
4: Lock means
41: Lock bar
42: Lifting part
43: Barrel lock
K: Drug solution preparing kit
P: Pre-filled syringe, drug solution-filled syringe
S: Solvent
M: Dry drug
V: Vial
L: Drug solution
T: Toxic drug
C: Infusion container

BEST MODES FOR CARRYING OUT THE INVENTION

With reference to the drawings, hereinafter, description will be given of a drug solution preparing kit according to the present invention. However, the invention of this application is not limited to embodiment examples shown in these drawings.

Figure 2:
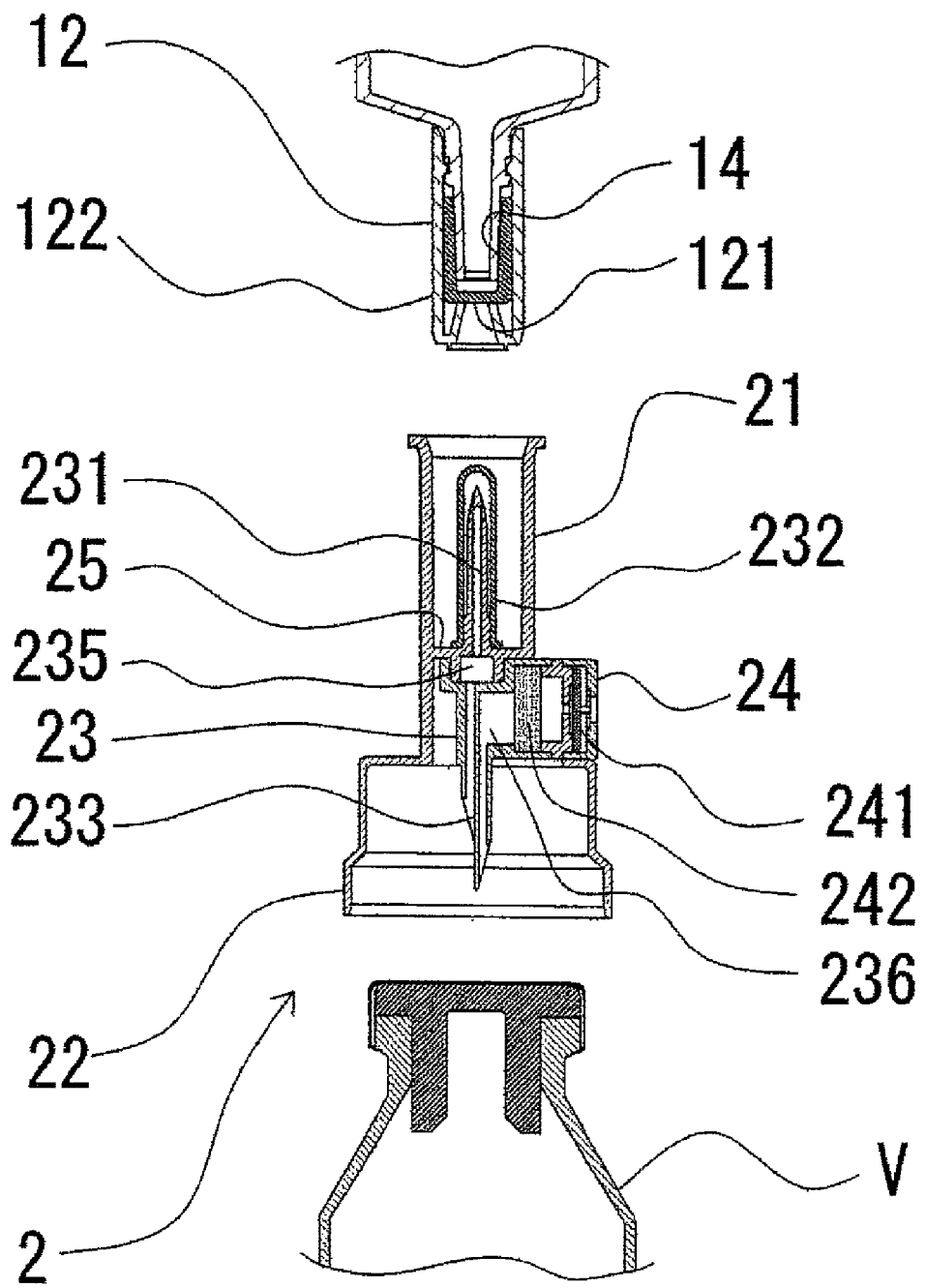
FIG. 2 is a partially enlarged vertical sectional view showing the drug solution preparing kit shown in FIG. 1 and an inlet of the vial.
Figure 3:
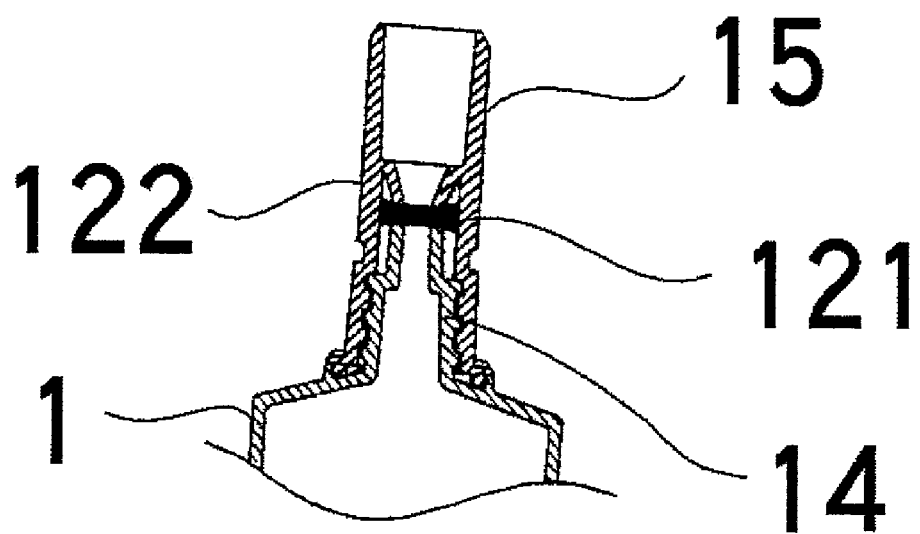
FIG. 3 is a vertical sectional view showing a tip end of a pre-filled syringe in which a hood is provided at a tip end of a sealing member.
Figure 4:
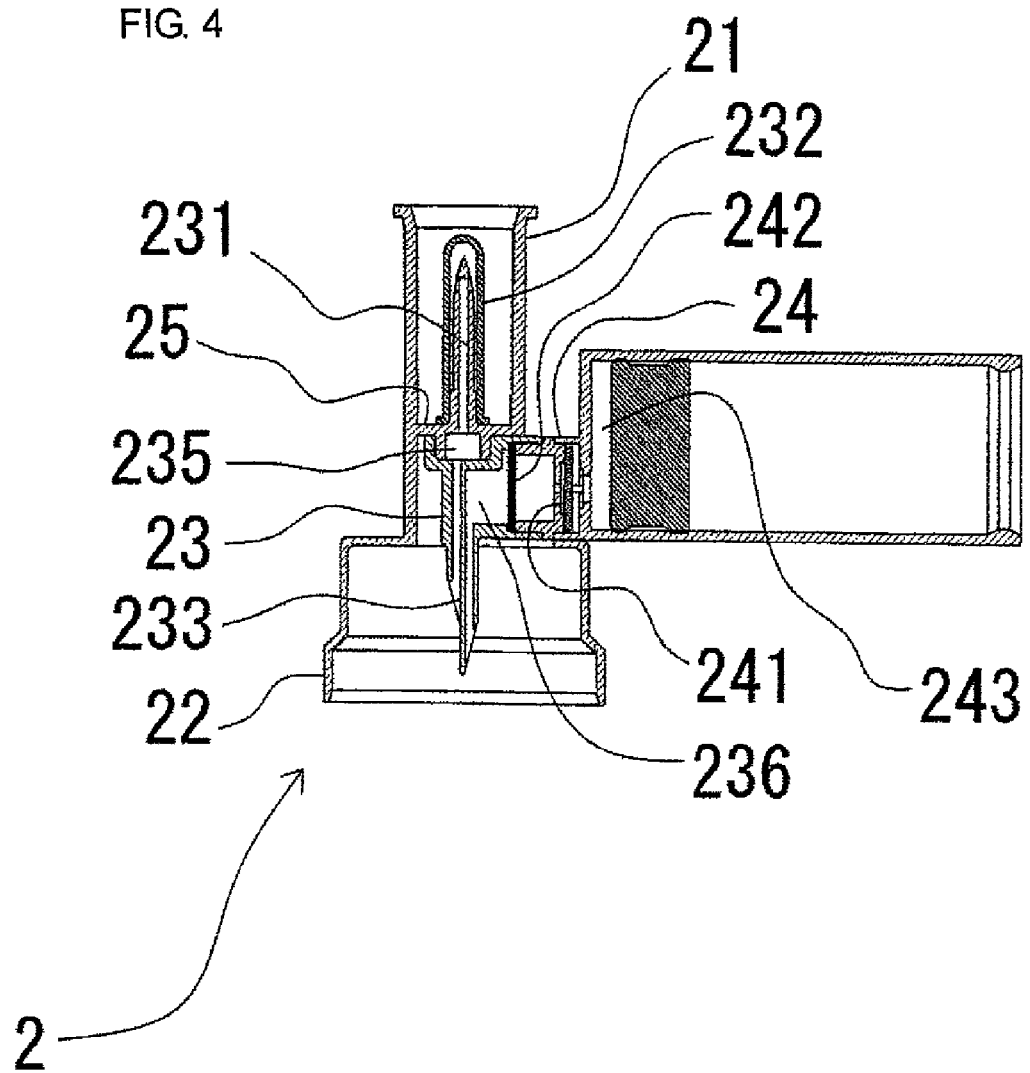
FIG. 4 is a vertical sectional view showing another embodiment example in a transfusing tool of the drug solution preparing kit according to the present invention.
Figure 5:
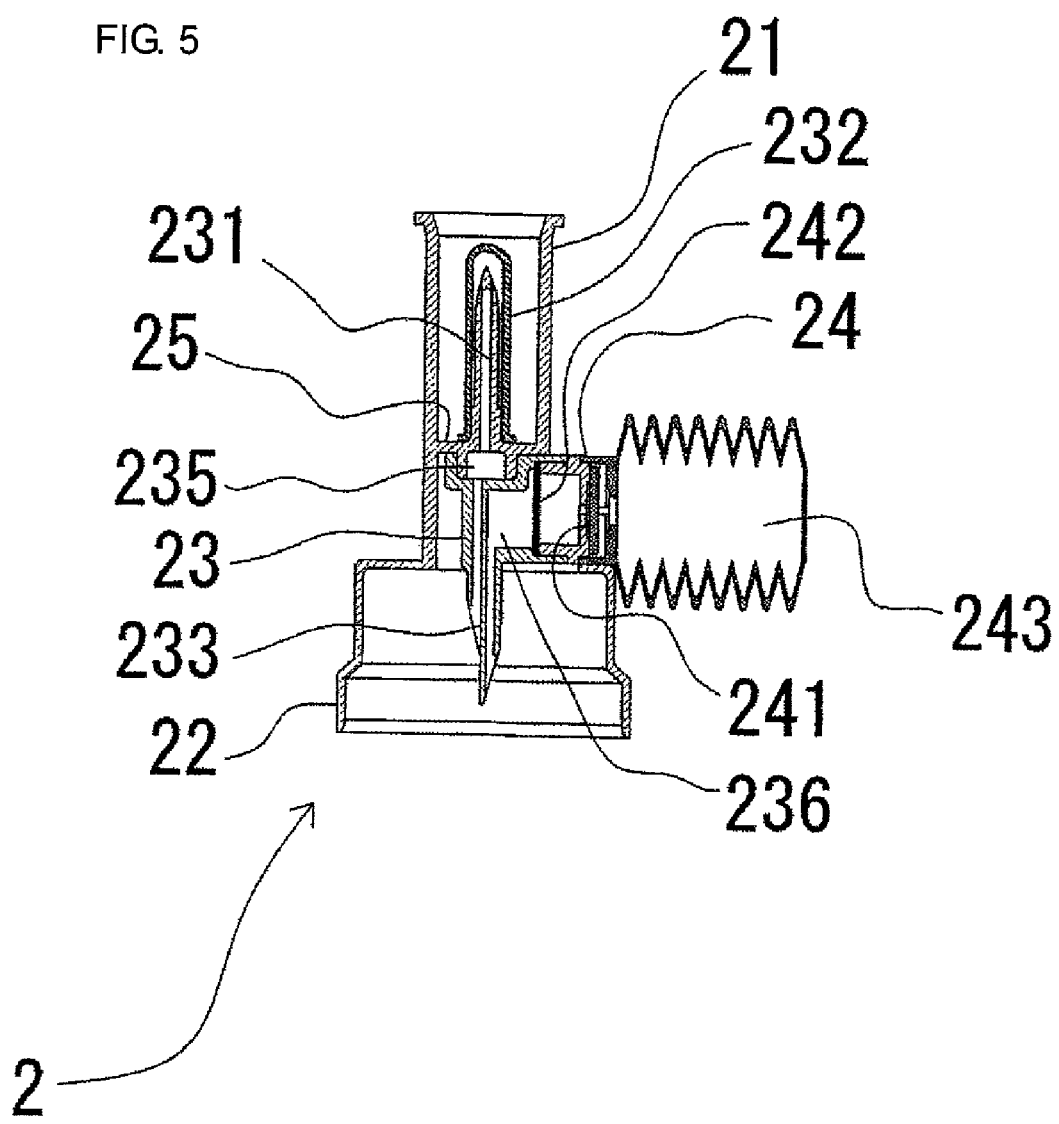
FIG. 5 is a vertical sectional view showing still another embodiment example in the transfusing tool of the drug solution preparing kit according to the present invention.
Figure 6:
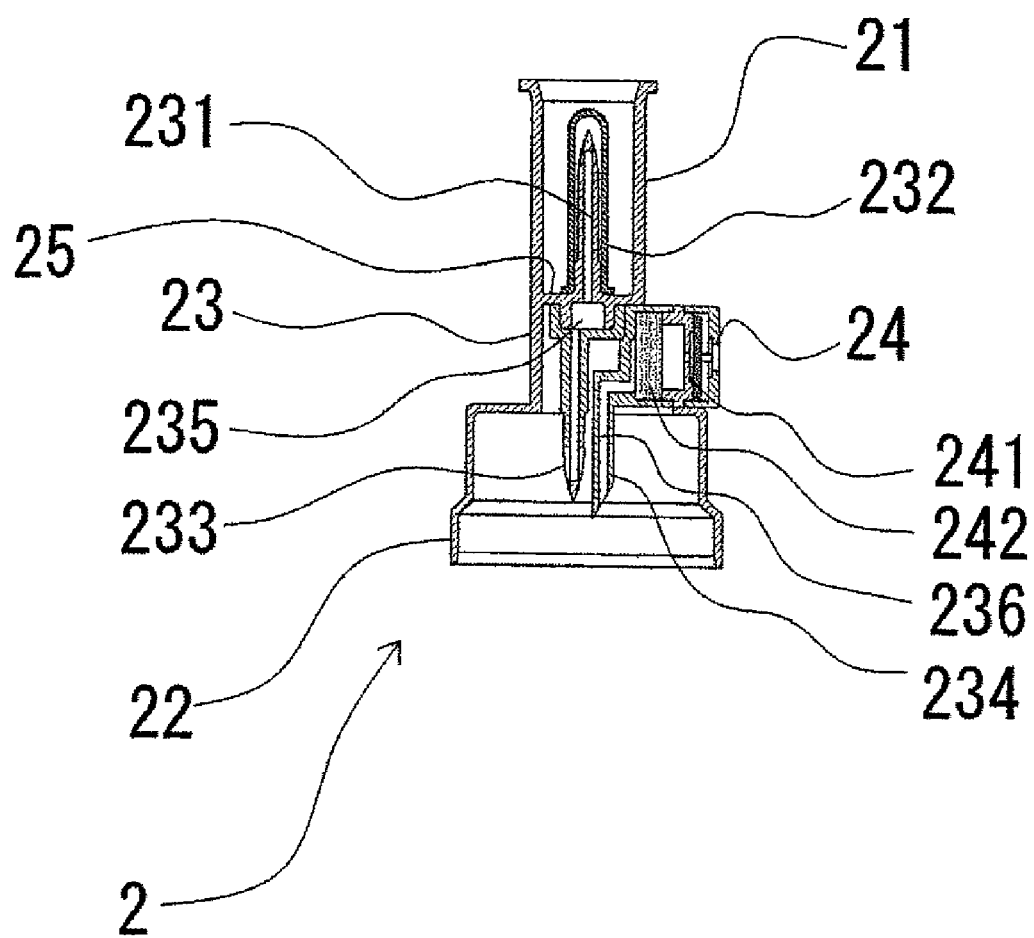
FIG. 6 is a vertical sectional view showing yet another embodiment example in the transfusing tool of the drug solution preparing kit according to the present invention.
Figure 7:
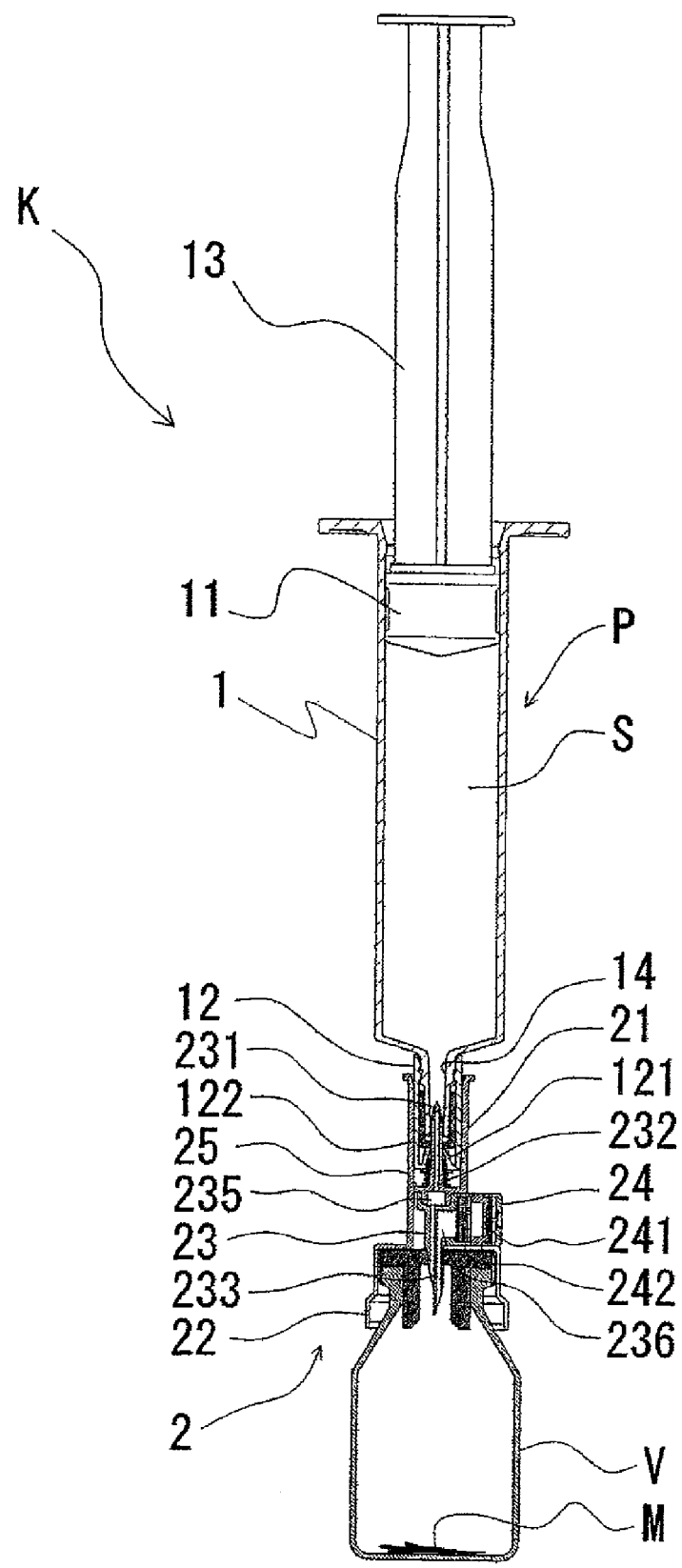
FIG. 7 is a vertical sectional view showing a state before preparation of a drug using the drug solution preparing kit shown in FIG. 1.
Figure 8:
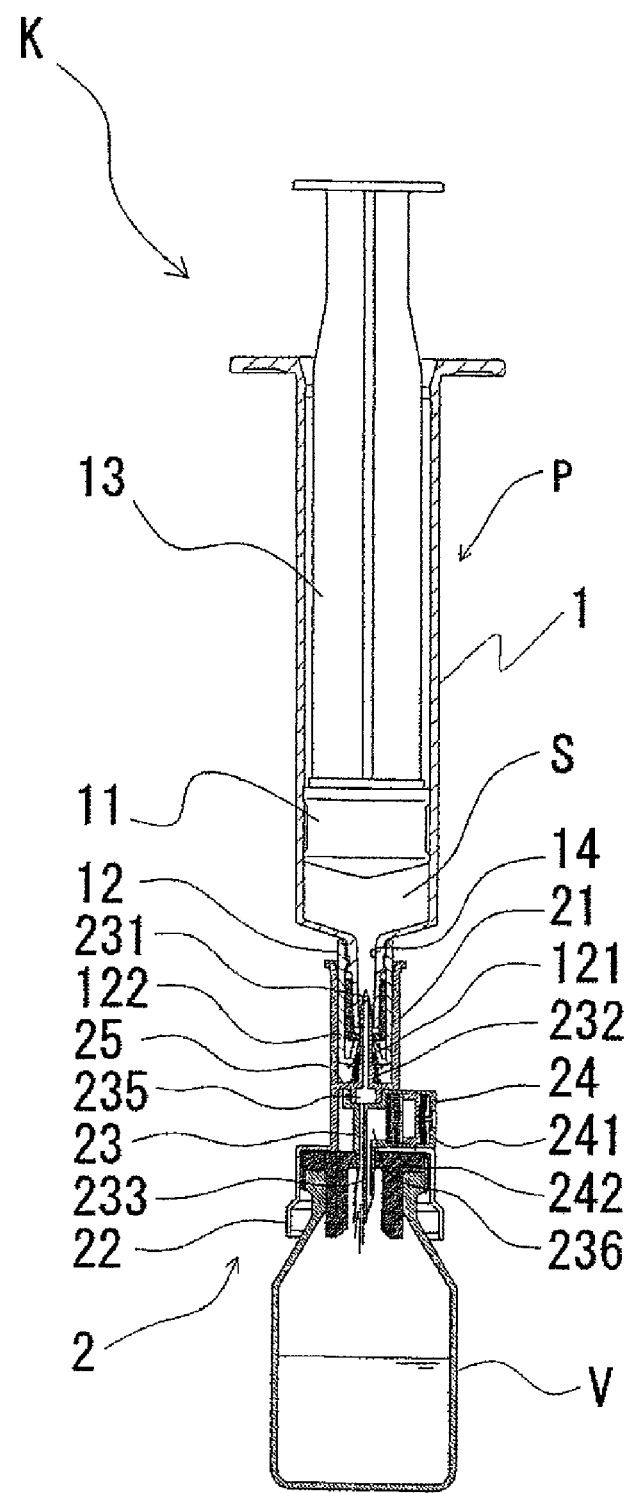
FIG. 8 is a vertical sectional view showing a state after preparation of the drug using the drug solution preparing kit shown in FIG. 1.
Figure 9:
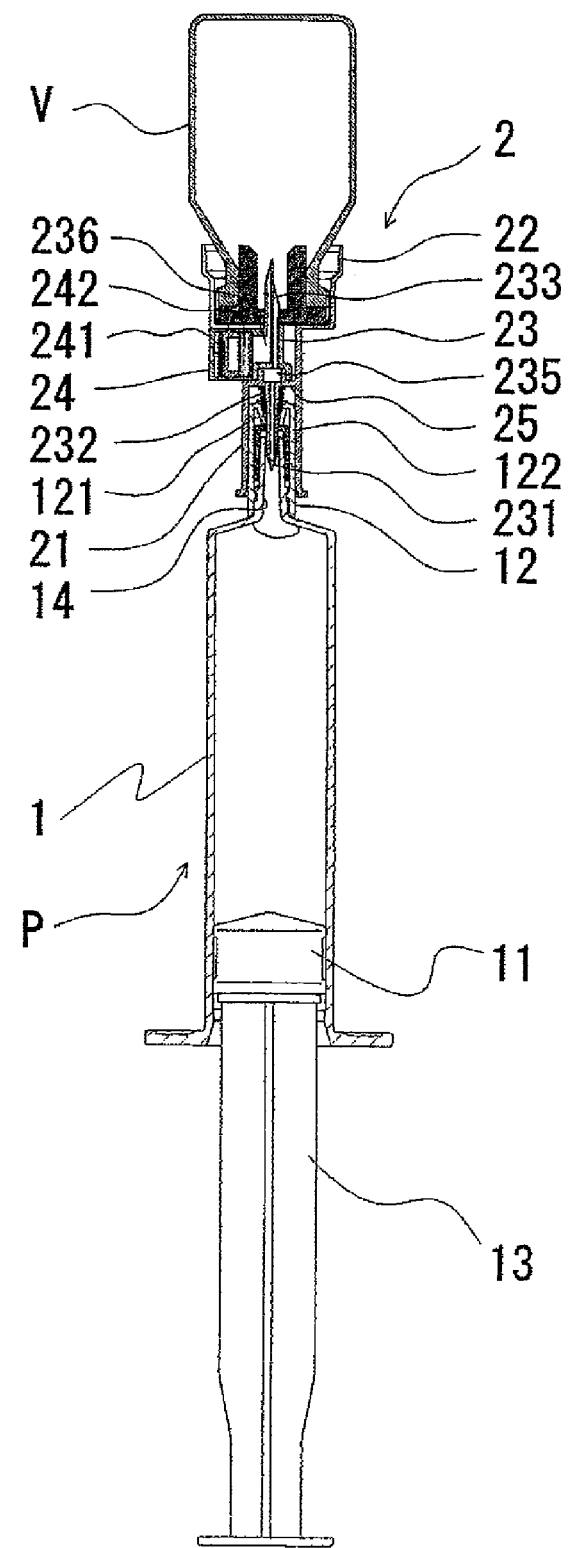
FIG. 9 is a vertical sectional view showing a state that the prepared drug is drawn into a barrel again in the drug solution preparing kit shown in FIG. 1.
Figure 10:
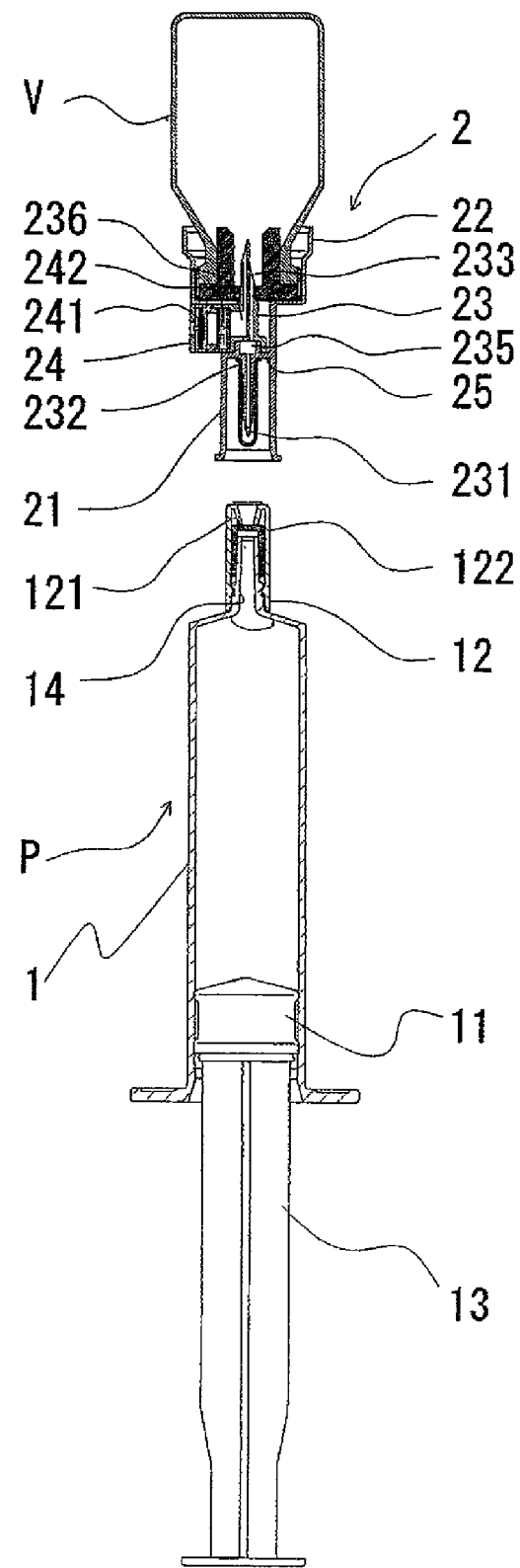
FIG. 10 is a vertical sectional view showing a state that the barrel into which the prepared drug solution is sealed is separated from the transfusing tool in the drug preparing kit shown in FIG. 1.

FIG. 1 is a vertical sectional view showing one embodiment example of a drug solution preparing kit according to the present invention which is mainly used for a vial. FIG. 2 is a partially enlarged vertical sectional view showing the drug solution preparing kit shown in FIG. 1 and an inlet of the vial. FIG. 3 is a sectional view showing a tip end of a pre-filled syringe in which a hood is provided at a tip end of a sealing member. FIG. 4 is a vertical sectional view showing another embodiment example in a transfusing tool of the drug solution preparing kit according to the present invention. FIG. 5 is a vertical sectional view showing still another embodiment example in the transfusing tool of the drug solution preparing kit according to the present invention. FIG. 6 is a vertical sectional view showing yet another embodiment example in the transfusing tool of the drug solution preparing kit according to the present invention. FIG. 7 is a vertical sectional view showing a state before preparation of a drug using the drug solution preparing kit shown in FIG. 1. FIG. 8 is a vertical sectional view showing a state after preparation of the drug using the drug solution preparing kit shown in FIG. 1. FIG. 9 is a vertical sectional view showing a state that the prepared drug is drawn into a barrel again in the drug solution preparing kit shown in FIG. 1. FIG. 10 is a vertical sectional view showing a state that the barrel into which the prepared drug solution is sealed is separated from the transfusing tool in the drug preparing kit shown in FIG. 1.

Figure 11:
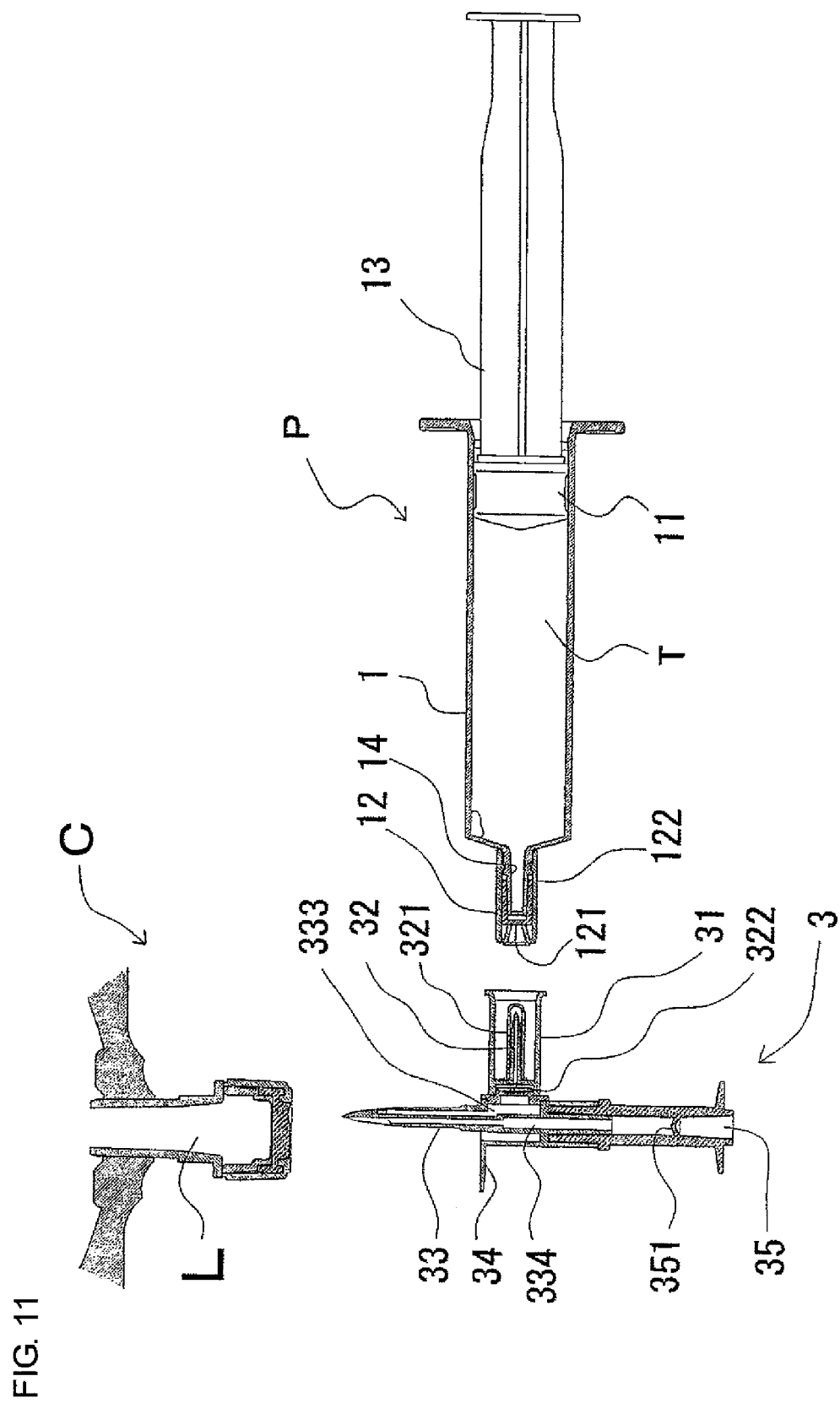
FIG. 11 is a vertical sectional view showing one embodiment example of a drug solution preparing kit according to the present invention which is used for an infusion container.
Figure 12:
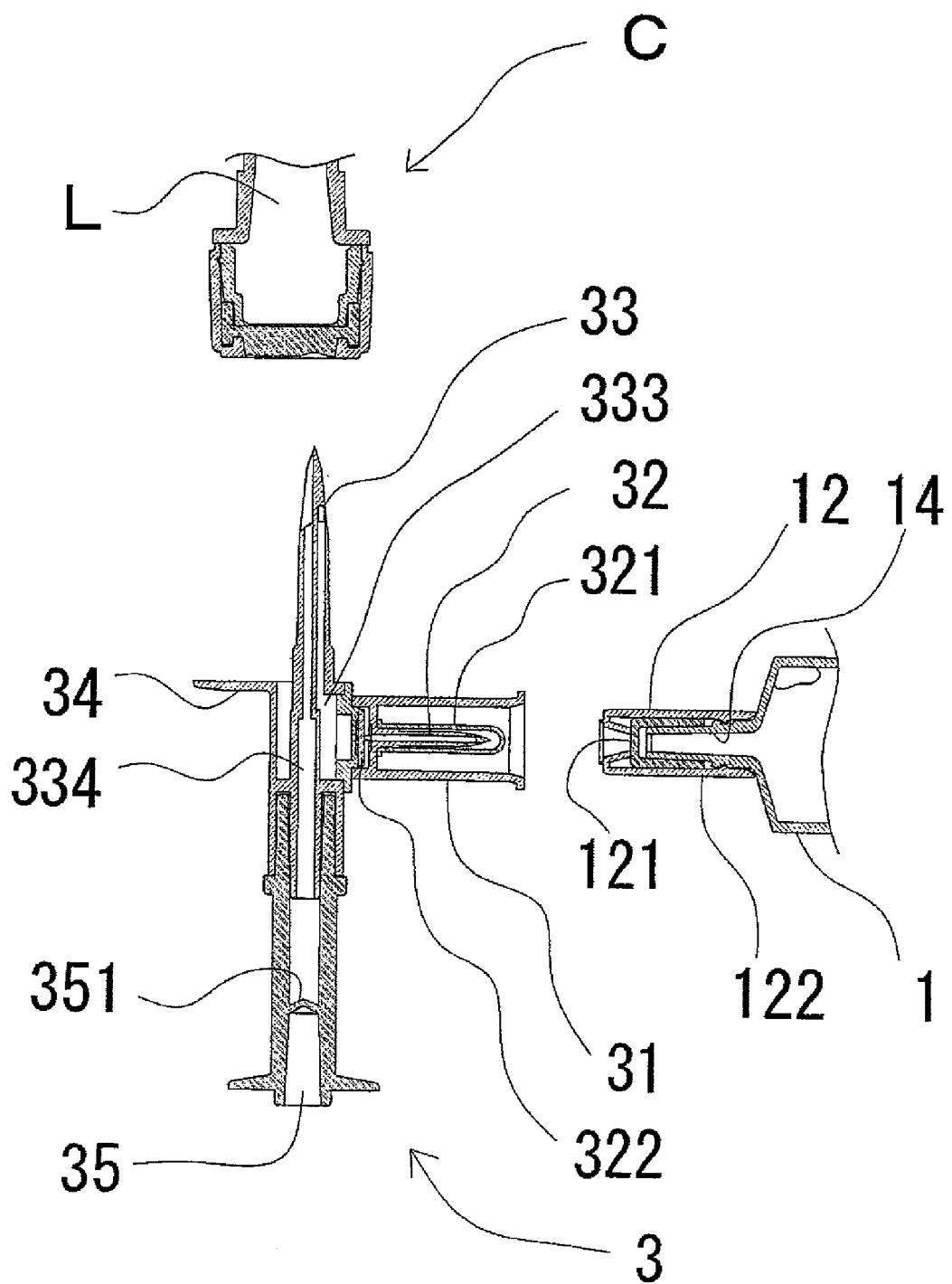
FIG. 12 is an enlarged vertical sectional view showing a transfusing tool, a tip end of a barrel, and an inlet of the vial each shown in FIG. 11.
Figure 13:
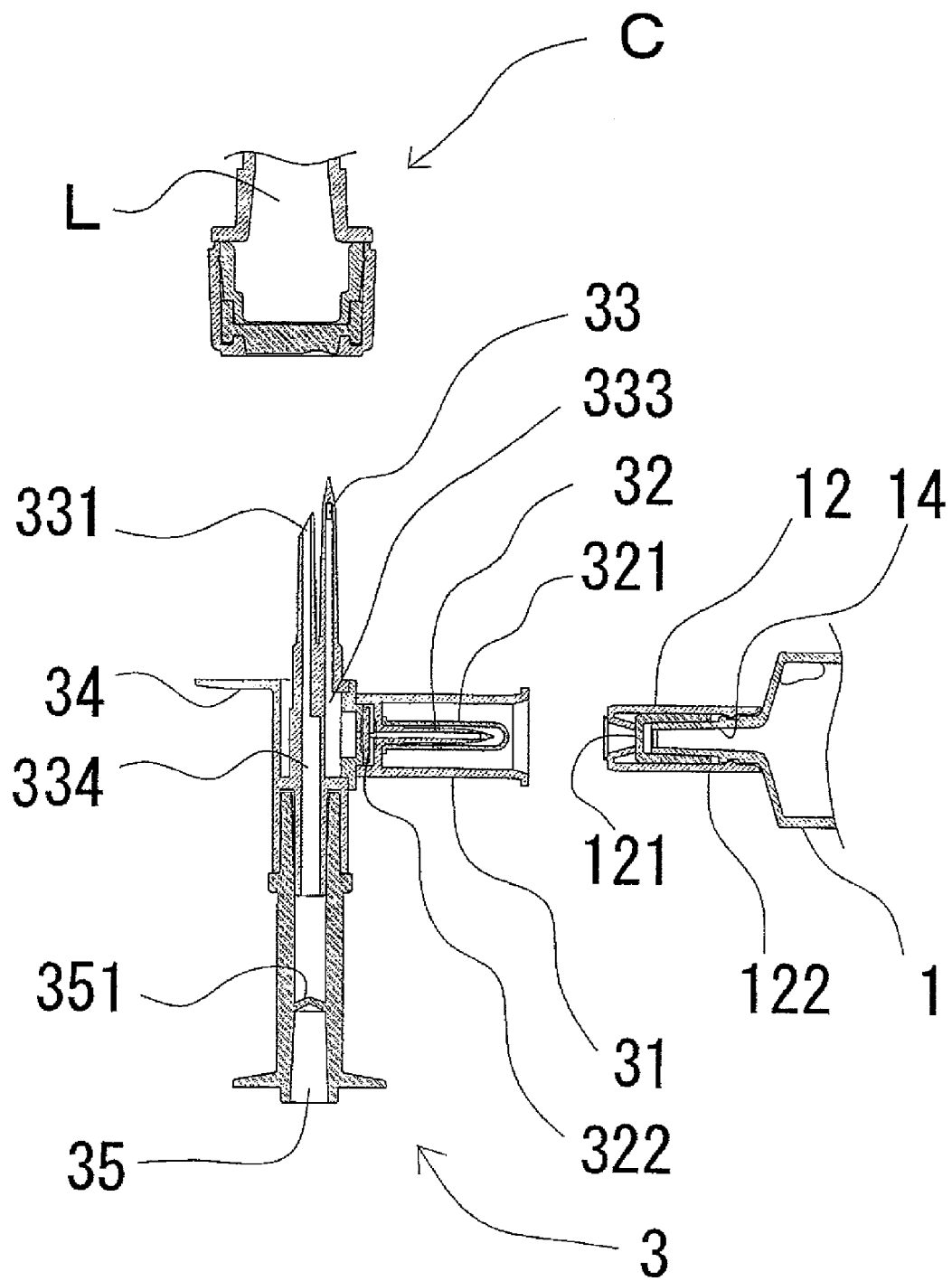
FIG. 13 is a vertical sectional view showing another embodiment example of the transfusing tool which is used for the infusion container.
Figure 14:
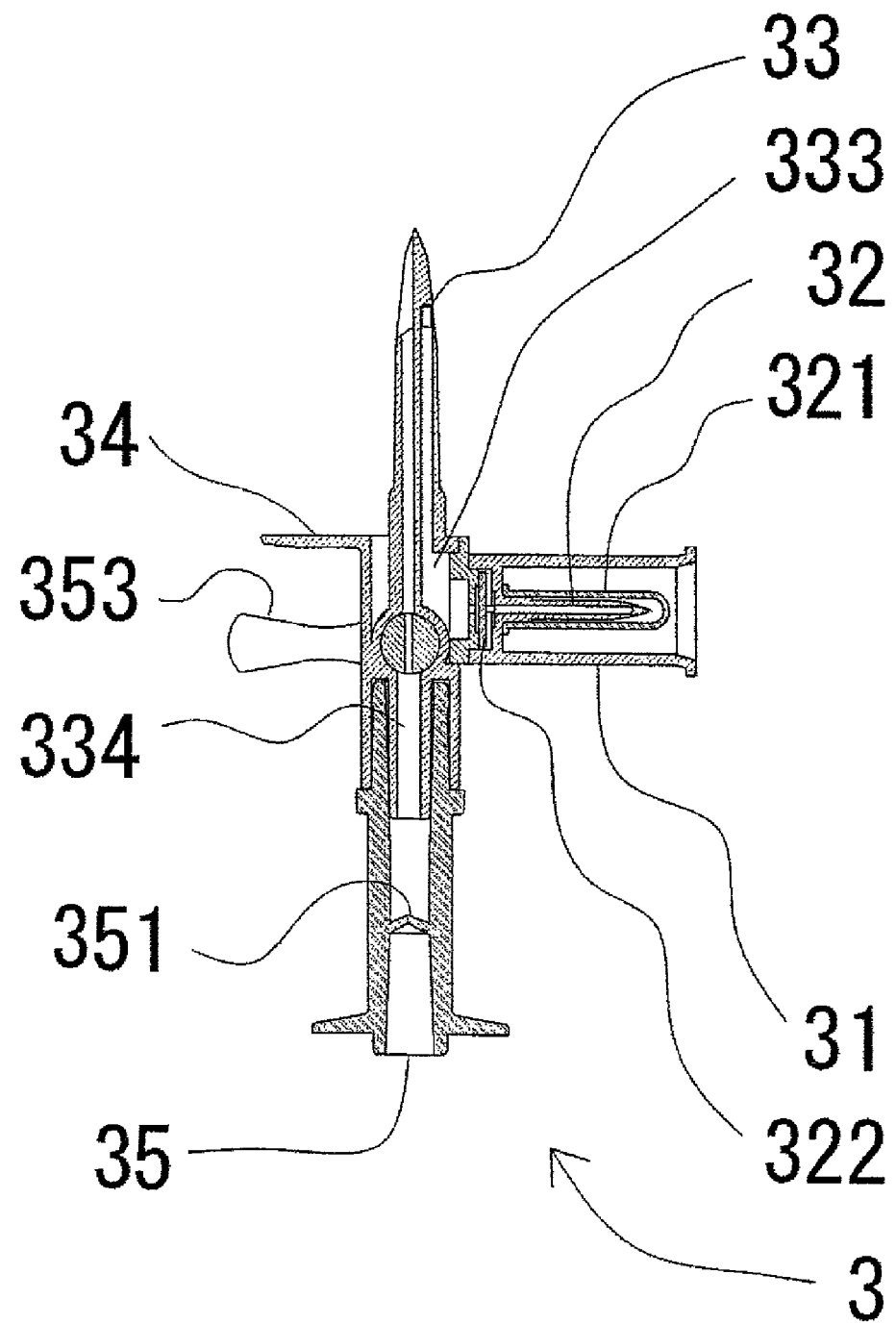
FIG. 14 is a vertical sectional view showing still another embodiment example of the transfusing tool which is used for the infusion container.
Figure 15:
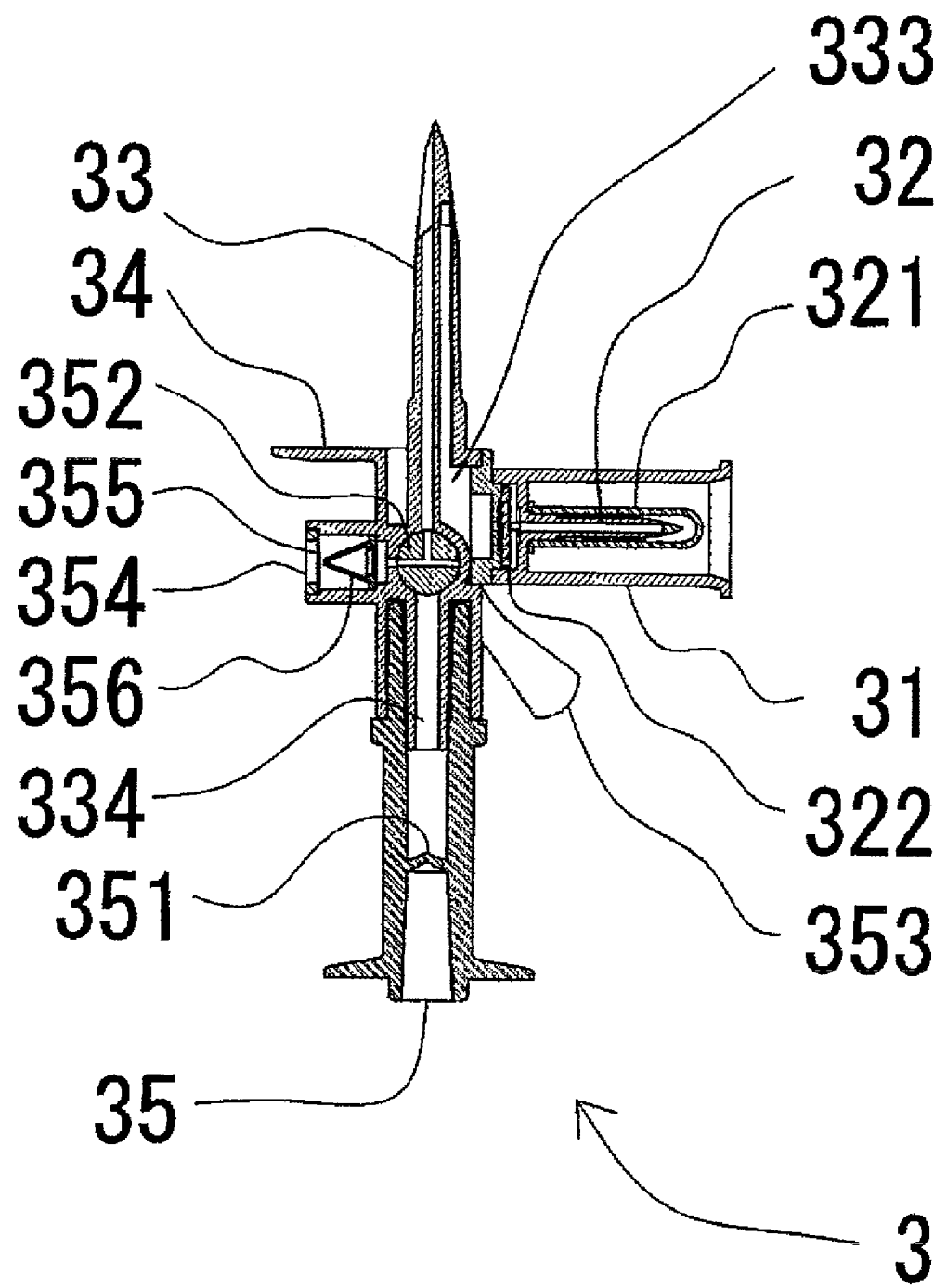
FIG. 15 is a vertical sectional view showing yet another embodiment example of the transfusing tool which is used for the infusion container.

FIG. 11 is a vertical sectional view showing one embodiment example of a drug solution preparing kit according to the present invention which is mainly used for an infusion container, and FIG. 12 is an enlarged vertical sectional view showing a transfusing tool, a tip end of a barrel, and an inlet of the vial each shown in FIG. 11. Moreover, FIG. 13 is a vertical sectional view showing another embodiment example of the transfusing tool which is mainly used for the infusion container. FIG. 14 is a vertical sectional view showing still another embodiment example of the transfusing tool which is mainly used for the infusion container. FIG. 15 is a vertical sectional view showing yet another embodiment example of the transfusing tool which is mainly used for the infusion container.

Figure 16:
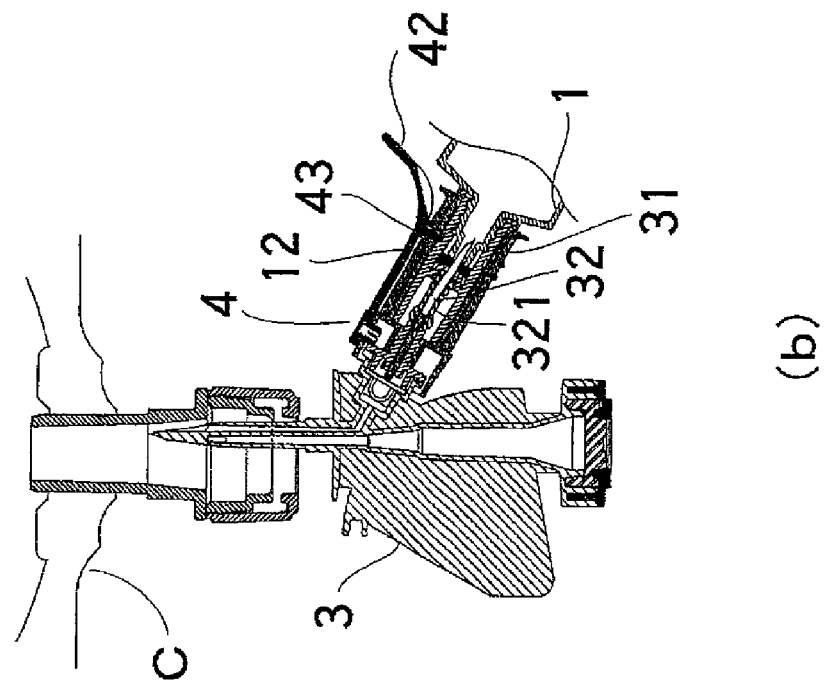
FIGS. 16(a) and 16(b) show one embodiment example of a lock means provided on the transfusing tool, respectively.
Figure 16:
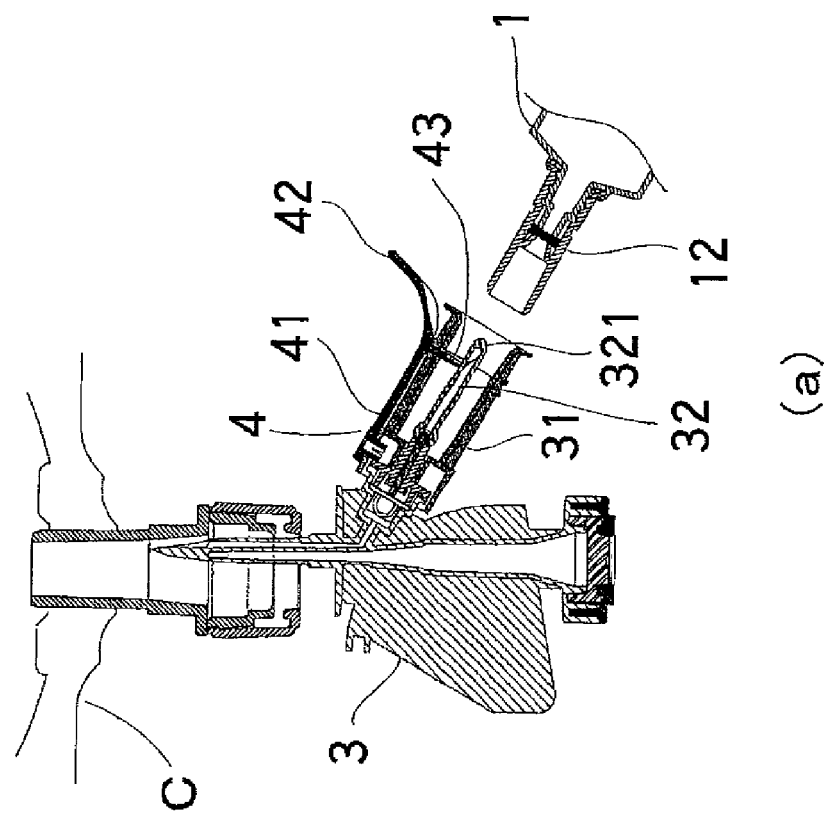

FIGS. 16(a) and 16(b) show one embodiment example of a lock means provided on the transfusing tool, respectively.

As shown in FIG. 1, a drug solution preparing kit K according to the present invention includes a pre-filled syringe P which is filled with a solvent S, and a transfusing tool 2 which attaches pre-filled syringe P to a vial V storing a drug, communicatively connects pre-filled syringe P to vial V, and mixes and dissolves the drug into and in the solvent.

Pre-filled syringe P has a cylindrical barrel 1 of which two ends are open. Barrel 1 has a tip end serving as a nozzle 14 to which a sealing member 12 including an elastic body film 121 and a caulking member 122 is attached. Sealing member 12 has a configuration that elastic body film 121 is attached to nozzle 14 by caulking member 122 in a liquid-tight manner and caulking member 122 can not be removed from nozzle 14. A gasket 11 is inserted into the rear end opening of barrel 1 in a liquid-tight manner and a slidable manner, and a plunger rod 13 is coupled to gasket 11. Barrel 1, sealing member 12 and gasket 11 form a space which is filled with solvent S.

Transfusing tool 2 is used for establishing communicative connection between the pre-filled syringe and the vial, and includes a partition wall 25 and a barrel attaching part 21 and a vial attaching part 22 which are provided at two sides of partition wall 25, respectively, with partition wall 25 being defined as a center. Barrel attaching part 21 has a first needle 231 provided thereinside, and first needle 231 can penetrate through elastic body film 121 of sealing member 12 of pre-filled syringe P when pre-filled syringe P is attached to barrel attaching part 21. First needle 231 is covered with a rubber cap serving as a covering member 232. Moreover, vial attaching part 22 has a second needle 233 provided thereinside so as to be coaxial with first needle 231, and second needle 233 can penetrate through a plug of vial V when vial V is attached to vial attaching part 22. First needle 231 and second needle 233 are communicatively connected to each other through a first communication channel 235. The second needle has a second communication channel 236 which is formed independently of first communication channel 234, and second communication channel 236 establishes communicative connection between second needle 233 and a port 24. Port 24 includes a one-way valve 241 which can discharge gas from the system in an irreversible manner, and a hydrophobic filter 242 which is provided at a side of a second communication part of one-way valve 241.

The drug preparing kit according to the present invention can be handled with ease. The port includes the one-way valve which can discharge only the gas from the system in the irreversible manner. Upon preparation of a drug, therefore, when the plunger is pushed into the barrel, the gas corresponding to the amount of the reduced volume in the system is discharged from the system. Then, when the prepared drug solution is drawn into the plunger, the pressure in the system is reduced. Thus, a splash of a hazard drug or an aerosol is not jetted outside the system. Moreover, the tip end of the pre-filled syringe, into which the prepared drug is sealed, is blocked with the sealing member, which can not be removed from the pre-filled syringe, in a liquid-tight manner, so that the drug solution is not leaked from the barrel. Therefore, the toxic drug is not exposed in an ambient environment upon preparation of the drug solution. Further, since the nozzle of the pre-filled syringe is blocked with the sealing member after preparation of the drug solution, there occurs no accident that a common injection needle is erroneously connected to the pre-filled syringe filled with the prepared drug solution in intravenous injection.

Barrel 1 is a cylindrical member having two open ends, that is, nozzle 14 which is a tip end and a base end. Normally, barrel 1 is made of glass or transparent plastic such as polypropylene, polyethylene, polymethylpentene or cyclic polyolefin. In barrel 1, nozzle 14 is sealed with sealing member 12 and the inner cavity on the base end side is sealed with gasket 11 inserted from the open base end. The space in barrel 1, which is defined by sealing member 12 and gasket 11, is filled with solvent S in advance. At the time when the space is filled with solvent S, preferably, the position of gasket 11 is located rearward on the base end side of barrel 1 such that a certain amount of gas can be drawn beyond a nominal volume upon preparation and re-suction of the drug solution.

As shown in FIG. 2, preferably, sealing member 12 consists of elastic body film 121 and caulking member 122. A material for elastic body film 121 must allow first needle 231 to penetrate therethrough and must maintain a liquid-tight property, and suitable examples thereof include natural rubber, synthetic rubber and thermoplastic elastomer. A material for caulking member 122 must have a firm fitting property or adhesion property such that caulking member 122 can not be removed from the tip end of the barrel and, also, must have a high initial coefficient of elasticity to a certain degree in order to maintain a liquid-tight property in cooperation with elastic body film 122. Examples of such a material include polypropylene, polycarbonate, aluminum and the like.

As shown in FIG. 3, moreover, an annular hood 15 may be provided at a tip end of caulking member 122. Hood 15 brings about the following advantage. That is, when drug solution-filled syringe P is attached to barrel attaching part 21, 31, a region where barrel attaching part 21, 31 overlaps with hood 15 increases. Thus, the drug solution-filled syringe can be stably attached to the transfusing tool without swaying. The hood preferably has a length in a range from 10 mm to 15 mm. As shown in FIG. 3, moreover, the hood and the caulking member may be integrated into one.

Normally, gasket 11 is inserted from the open base end side of cylindrical barrel 1 in a slidable manner and, therefore, is formed into a column shape. Herein, gasket 11 has a thickness which is not less than a level so as not to tilt with ease after being inserted, has annular ribs which are formed at tip and base ends and are slightly larger than a diameter of an inner peripheral wall of the barrel, and has a diameter which is slightly smaller than that of the inner peripheral wall of the barrel. Moreover, gasket 11 has an inner cavity which is formed with a female screw so as to receive plunger 13 which is formed with a male screw at its tip end, and is arranged so as to maintain the liquid-tight property when plunger 13 is moved. Elastic body film 121 is formed into a thin shape so as to allow first needle 231 of transfusing tool 2 to readily penetrate therethrough without loss of the liquid-tight property when first needle 231 penetrate through or is removed from elastic body film 121. A material for gasket 11 or elastic body film 121 largely depends on compatibility with a medicine to be stored, and desirable examples thereof include natural rubber, butyl rubber, styrene butadiene rubber, thermoplastic elastomer and the like. As solvent S, moreover, a physiological saline or a glucose solution is used normally.

First needle 231 is a syringe connecting needle, is covered with a covering member 232, and preferably has a liquid-tight property that prevents the toxic drug from being leaked when first needle 231 penetrates through or is removed from elastic body film 121 of the barrel. Covering member 232 is made of an elastic body which has a certain degree of flexibility and is high in restoring property. Suitable examples of the elastic body include natural rubber and synthetic rubber each of which is excellent in liquid-tight property and re-sealing property. Moreover, first needle 231 is made of a material which can readily penetrate through elastic body film 121 of sealing member 12 attached to nozzle 14 and is readily covered with covering member 232 upon removal of the barrel. Examples of the material include stainless steel, ABS resin, BS resin, polycarbonate and polystyrene.

Second needle 233 can readily penetrate through a rubber plug for the inlet of the vial, and is preferably a rocket needle having no pinhole at its axial center in order to prevent generation of an aerosol, which floats for a long period of time, as much as possible when solvent S is introduced into vial V while being directed jetted to dry drug M or a liquid surface. Also preferably, an opening for introduction of the solvent is appropriately set at a position for reducing a remaining amount of the drug solution when the drug solution is sucked into the barrel again. Suitable examples of a material that satisfies the performance described above include ABS resin, BS resin, polycarbonate and polystyrene.

Preferably, barrel attaching part 21 is provided with a protruding piece or a lock mechanism for caulking barrel 1 slightly in order to prevent a disadvantage that barrel 1 attached to barrel attaching part 21 sways when being handled, a clearance is formed at a peripheral edge of the needle and the toxic drug is exposed. Also preferably, the tip end of barrel attaching part 21 is farther in position than the tip end of first needle 231 within a range that first needle 231 is pushed into barrel 1 so as to be communicatively connected to barrel 1 in order to prevent disadvantages that a user is injured by first needle 231 and that the user suffers from exposure to a slight amount of the toxic drug remaining in covering member 232.

Preferably, vial attaching part 22 is provided with a protruding piece or a lock mechanism for caulking vial V slightly in order to prevent a disadvantage that vial V attached to vial attaching part 22 sways when being handled, a clearance is formed at a peripheral edge of the needle and the toxic drug is exposed. More preferably, in a case where covering member 232 covers first needle 231, vial attaching part 22 is provided with a mechanism such as an engagement claw engaged with a neck portion of the vial such that the vial can not be removed from vial attaching part 22 once being attached to vial attaching part 22. Also preferably, the tip end of vial attaching part 22 is farther in position than the tip end of second needle 233 so as to prevent loss of a liquid-tight property in a case where vial V is attached to vial attaching part 22 with a center of vial attaching part 22 being displaced from a center of second needle 233.

In port 24 of transfusing tool 2, one-way valve 241 is communicatively connected to an opening of second communication channel 236, which is opposed to second needle 233, and allows discharge of gas in the system.

When plunger 13 is pushed with vial V being located at a down side so that solvent S in barrel 1 is introduced into vial V, one-way valve 241 receives an internal pressure applied in vial V and discharges the gas from the system through second communication channel 236. Second communication channel 236 acts as a gas discharge path. Therefore, even when plunger 13 is pulled with vial V being located at an up side so that the drug solution prepared by dissolving and mixing is sucked and collected, the gas never returns to vial V. In order to prevent a disadvantage that the drug solution is leaked outside the system through one-way valve 241, moreover, a hydrophobic filter 242 is provided so as to adjoin to the second communication channel of one-way valve 241. Hydrophobic filter 242 is made of water repellent resin such as polytetrafluoroethylene or ethylene-tetrafluoroethylene, or resin or fiber having a surface subjected to water repellent treatment.

With regard to the hydrophobic filter, a pore diameter, a structure and a thickness are selected appropriately. However, an aerosol floating for a long period of time typically has a size in a range from about 10 nm to about 50 nm. In consideration of an electrostatic property and the like, a complex combination of a hydrophilic filter, a positively or negatively charged filter, an activated carbon and the like may be used as a filter.

In place of the complex combination of the filters, further, a chamber 243 may be provided in a fluid-tight manner so as to prevent discharge of the aerosol from the system, which can achieve satisfactory prevention against the exposure. A shape of chamber 243 can be selected appropriately as long as chamber 243 can be expanded or deformed so as to readily increase an inner volume. As shown in FIG. 4, chamber 243 may be formed into a cylinder shape such that the tip end is connected to port 24 in a fluid-tight manner and a chamber gasket is attached in a slidable manner at a position spaced away from a base end side by a predetermined distance. As shown in FIG. 5, alternatively, chamber 243 may be formed into a bellows shape or may be formed as a bag-shaped film (not shown).

In any cases of provision of the various chambers, consideration must be given to a load against a change in inner volume. For example, in the case where the chamber is formed into the cylinder shape to which chamber gasket is attached, a sectional area of the chamber gasket is made large such that the chamber gasket slides with smaller pressurization. In the case where the chamber is formed into the bellows shape or is formed as the film, a material of the chamber to be selected herein must be high in flexibility or must be thin.

As another embodiment, second needle 233 having first communication channel 235 and a third needle 234 having second communication channel 236 may be provided on vial attaching part 22 as shown in FIG. 6, in addition to first communication channel 235 or second communication channel 236 provided on second needle 233 independently of each other. In consideration of a fact that an anti-cancer drug, particularly, an absolute ethanol or the like causes formation of cracks at a plastic portion or a joint portion, preferably, a double-ended needle, in which the first needle and the second needle are integrated into one, is provided without provision of the third needle. Also preferably, the double-ended needle is made of stainless steel.

Next, description will be given of use of the drug solution preparing kit according to the present invention.

First, vial V is inserted into vial inserting part 21 of transfusing tool 2 with the inlet side thereof being directed upward. Next, in a state that vial V is stably placed on a desk with the bottom side thereof being directed downward, barrel 1 is attached to barrel attaching part 21 of transfusing tool 2 with the tip end side being directed downward (see FIG. 7). In the state that the vial V is located at the lower side, when the plunger 13 is pushed downward slowly, solvent S in barrel 1 is introduced into vial V and then is jetted to the inner wall of vial V. Concurrently, the gas in vial V is discharged to the port through needle 233 provided on the vial attaching part side. Thus, the solvent in barrel 1 is transfused into vial V. When drug solution preparing kit K is shaken, the drug is dissolved in the solvent, so that a drug solution is prepared (see FIG. 8). Subsequently, plunger rod 13 is pulled so that the drug solution is sucked into and collected by barrel 1 up to the nominal volume (see FIG. 9). Then, transfusing tool 2 is removed from barrel 1 (see FIG. 10). Preferably, the position of gasket 11 herein is located rearward on the base end side as compared with the position when gasket 11 is filled with solvent S. With this configuration, the pre-filled syringe can be removed in the state that the pressure in the system is reduced. Therefore, even when a leakage such as a splash occurs or an aerosol generates, the occurrence or the generation is caused toward the interior of the vial. Therefore, dispersion of the drug solution to the ambient environment can be avoided.

Herein, when a dedicated transfusion needle (not shown) is connected to the tip end of barrel 1, the drug solution can be coinfused into a drip container as it is.

As described above, the drug can be prepared in such a manner that the pre-filled syringe is attached to the barrel attaching part, the vial is attached to the vial attaching part and the plunger is pushed/pulled. Moreover, no substance outside the system is mixed. Therefore, the drug can be prepared by a substantially aseptic and simple process. In addition, the port is provided with the one-way valve capable of discharging only the gas from the system in the irreversible manner. Thus, upon preparation of the drug, when the plunger is pushed, the gas corresponding to the amount of the reduced volume in the system is discharged from the system. Then, when the prepared drug solution is drawn into the plunger, the pressure in the system is reduced. As a result, the splash of the hazard drug or the aerosol is not jetted outside the system. Further, the tip end of the pre-filled syringe, into which the prepared drug is sealed, is blocked with the sealing member, which can not be removed from the tip end, in the liquid-tight manner. Therefore, this configuration can prevent the leakage of the drug solution from the barrel and can prevent erroneous connection of a common needle in intravenous injection.

With reference to FIG. 11, next, description will be given of a drug solution preparing kit for use in an infusion container. A drug solution-filled syringe is identical in shape with the pre-filled syringe described above; therefore, description of the shape will not be given here. Drug solution preparing kit K includes drug solution-filled syringe P filled with a toxic drug T, and a transfusing tool 2 for establishing communicative connection between pre-filled syringe P attached thereto and infusion container C storing a drug solution L and mixing and dissolving toxic drug T with and in drug solution L.

Drug solution-filled syringe P is filled with toxic drug T.

In transfusing tool 3, when a direction that a needle penetrates through a plug body of infusion container C is defined as an axis, a second needle 33 is formed at an upper end, an outlet port 35 is formed at a lower end, and a cylinder-shaped barrel attaching part 31 is formed so as to protrude in a direction perpendicular to the axis. At an axial center position of barrel attaching part 31, a first needle 32 is formed so as to penetrate through an elastic body film 121 of a sealing member 12, which is provided at a tip end of the barrel, when drug-filled syringe P is attached to the barrel attaching part. First needle 32 is covered with a rubber cap serving as a covering member 321. A first communication channel 333 and a second communication channel 334 are formed in second needle 33 independently of each other. First communication channel 333 is communicatively connected to first needle 32 and second communication channel 334 is communicatively connected to outlet port 35. First communication channel 333 is provided with a one-way valve 322 that allows communication of only a fluid flowing from a direction of the first needle. Outlet port 35 is provided with a blocking member 351 through which a bottle needle of an infusion line can penetrate. At a position of a base end of the second needle, moreover, a flange 34 is provided in order to allow second needle 33 to penetrate through the infusion container and to allow second needle 33 to be secured stably to the infusion container in a liquid-tight manner.

Drug-filled syringe P filled with toxic drug T may be a pre-filled syringe filled with a toxic drug in advance or a syringe filled with a drug prepared by the kit described above.

First needle 32 is covered with covering member 321, and has a liquid-tight property that prevents the toxic drug from being leaked when first needle 32 penetrates through or is removed from elastic body film 121 of the barrel. First needle 32 is made of a material which can readily penetrate through elastic body film 121 of sealing member 12 attached to nozzle 14 and can be readily re-sealed with covering member 321 upon removal of the barrel. Examples of the material include stainless steel, ABS resin, BS resin, polycarbonate, polystyrene and the like. Moreover, covering member 321 is made of an elastic body which has a certain degree of flexibility and is high in restoring property. Suitable examples of the elastic body include natural rubber and synthetic rubber each of which is excellent in liquid-tight property and re-sealing property.

Second needle 33 can readily penetrate through the plug body of the infusion container. Preferably, an opening for introduction of the liquid drug is set such that an opening of the first communication channel and an opening of the second communication channel are spaced away from each other appropriately in order to help dilution in the infusion container. For example, second needle 33 is preferably a rocket needle having no pinhole at its axial center. Suitable examples of a material that satisfies the performance described above include ABS resin, BS resin, polycarbonate, polystyrene and the like.

As shown in FIG. 11, the first communication channel and the second communication channel are formed in the second needle independently of each other. As shown in FIG. 12, alternatively, second needle 33 and third needle 331 may be formed such that axes thereof are directed in a single direction, first communication channel 333 may be formed in second needle 33 and second communication channel 334 may be formed in third needle 331.

Preferably, barrel attaching part 31 is provided with a protruding piece or a lock mechanism for caulking barrel 1 slightly in order to prevent a disadvantage that barrel 1 attached to barrel attaching part 31 sways when being handled, a clearance is formed at a peripheral edge of the needle and the toxic drug is exposed. Also preferably, a tip end of barrel attaching part 31 is farther in position than a tip end of covering member 321 within a range that the first needle is pushed into barrel 1 so as to be communicatively connected to barrel 1 in order to prevent disadvantages that a user is injured by first needle 32 and that the user suffers from exposure to the toxic drug by a touch.

Outlet port 35 of transfusing tool 3 is communicatively connected to second communication channel 332 formed in second needle 331, and is blocked with blocking member 351 so as to be open when being connected to the infusion line. Blocking member 351 allows the bottle needle of the infusion line to penetrate therethrough, and is typically formed into an elastic thin film shape in order to prevent the penetrating bottle needle from being readily removed therefrom and to prevent loss of the liquid-tight property. In consideration of the compatibility with a medicine to be in contact with blocking member 351, appropriate examples of a material that satisfies the performance described above include natural rubber, butyl rubber, chlorinated butyl rubber, styrene butadiene rubber, thermoplastic elastomer and the like. Moreover, the opening of the outlet port 35 is preferably formed into a cylindrical shape having an inner diameter which is slightly smaller than the bottle needle in order to help holding of the bottle needle of the infusion line. As shown in FIG. 13, further, second communication channel 334 may be provided with a stopcock 353 for completely avoiding the exposure to the toxic drug such that the communicative connection to the port can be switched in a freely open/close manner.

In a case where a large amount of toxic drug T in barrel 1 must be infused into infusion container C, the pressure in infusion container V is increased and then is turned into a positive pressure. As a result, there is a possibility that a drip speed becomes faster than an assumed speed. In order to avoid such a disadvantage, the positive pressure must be relaxed in such a manner that the gas is discharged from infusion container C. As shown in FIG. 14, preferably, a branched part 352 is provided on second communication channel 334 and a discharge port 354 having a one-way valve 356 and a hydrophobic filter 355 is communicatively connected to branched part 352. Herein, hydrophobic filter 355 provided on discharge port 354 exerts no harm upon discharge of the gas in the infusion container, and has a sectional area to a degree that permeation is not hindered even when hydrophobic filter 355 is covered with a membrane-shaped drug solution in the infusion container. Examples of a material of hydrophobic filter 355 include water repellent resin such as polytetrafluoroethylene or ethylene-tetrafluoroethylene, or resin or fiber having a surface subjected to water repellent treatment. With regard to hydrophobic filter 355, a pore diameter, a structure and a thickness are selected appropriately. However, an aerosol floating for a long period of time typically has a size in a range from about 10 nm to about 500 nm. In consideration of an electrostatic property and the like, a complex combination of a hydrophilic filter, a positively or negatively charged filter, an activated carbon and the like may be used as a filter. In place of the complex combination of the filters, further, a chamber (not shown) may be provided on the discharge port in a fluid-tight manner so as to prevent discharge of the aerosol from the system, which can achieve satisfactory prevention against the exposure. Moreover, the provision of the one-way valve prevents flow of external gas into the system and allows discharge of the gas in an aseptic manner.

Further, branched part 352 is provided with stopcock 353 capable of switching between the communicative connection from second communication channel 334 to outlet port 35 and the communicative connection from second communication channel 334 to discharge port 354. Therefore, actuation of the stopcock allows avoidance of an unintentional change in drip speed due to a factor that the solution is pushed toward the infusion line in drip administration.

A lock means 4 is preferably provided for preventing the drug solution-filled syringe from being removed from barrel attaching part 31 due to inevitable reasons. As shown in FIG. 16(a), for example, lock means 4 includes a lock lever 41 having a lifting part 42 of which a base end is formed into an upwardly warped shape with respect to the barrel attaching part, and a barrel lock 43 formed at the base end of lifting part 42. As shown in FIG. 16(b), when drug solution-filled syringe P is attached to barrel attaching part 31, the barrel lock is engaged with the base end of sealing member 12. Since sealing member 12 is provided so as not to be removed from barrel 1, drug solution-filled syringe P is not removed from barrel attaching part 31. After the infusion container is filled with the drug solution, the syringe can be removed from the barrel attaching part in such a manner that the lifting part is lifted up.

Next, description will be given of use of the drug solution preparing kit according to the present invention. First, second needle 33 of transfusing tool 3 is communicatively connected to infusion container V. Then, a point of the needle is directed perpendicularly to a plug body of infusion container V such that the second needle is connected stably in a liquid-tight manner, and penetrates through the plug body until the infusion container comes into contact with flange 34. Next, barrel 1 is attached to barrel attaching part 21 of transfusing tool 2 with the tip end thereof being directed frontward. When plunger 13 is pushed slowly as it is, toxic drug T in barrel 1 is introduced into the infusion in infusion container V. After infusion of a required amount of toxic drug T, barrel 1 is removed from barrel attaching part 31. Thus, toxic drug T in barrel 1 is transfused into infusion container V. When infusion container V is shaken slightly, the drug solution to be used in drip injection is prepared by mixing and diluting. Subsequently, when the bottle needle of the infusion line is connected to outlet port 35, the drip administration can be preformed continuously while avoiding a leakage such as a splash or dispersion of an aerosol to an ambient environment.

Herein, the sealing member, through which the first needle has penetrated, is rapidly blocked by the rubber elastic property when being removed from the barrel attaching part, which can prevent a leakage of the drug solution remaining in the barrel. Moreover, since the first needle coming into contact with the toxic drug is covered in such a manner that the shape of the rubber cap is restored, there is no possibility that a user touches the toxic drug. In the infusion container into which the toxic drug is infused and to which the transfusing tool is attached, further, the one-way valve prevents backflow on the first communication channel side and the bottle needle is connected to the outlet port in the liquid-tight manner on the second communication channel side. Therefore, there is no risk of external exposure of the hazard drug in the infusion container to which the drug-filled syringe and the transfusing tool are connected.

As described above, the second needle penetrates through the plug body of the infusion container, the drug-filled syringe penetrates through the barrel attaching part, and the plunger is pushed, so that the drug solution can be prepared by mixing and diluting. Moreover, no substance outside the system is mixed. Therefore, the drug solution can be prepared by a substantially aseptic and simple process. In addition, the one-way valve that permits only infusion of the liquid drug is provided at the base end side of the first needle and the first needle is provided with the covering member, so that a temporary low pressure state at an instant that the connection is cancelled while a back pressure from the infusion container is eliminated upon removal of the pre-filled syringe is relaxed considerably. This configuration prevents occurrence of the leakage of the toxic drug from the connection portion and generation of the splash. After preparation of the drug solution, further, the tip end of the syringe is blocked in the liquid-tight manner with the sealing member which can not be removed from the syringe. Therefore, there is no possibility that the liquid drug remaining in the barrel is leaked slightly. Further, there is no malpractice that a common needle is used upon intravenous injection during a period from the open to the discarding.

INDUSTRIAL APPLICABILITY

As described above, the drug solution preparing kit according to the present invention includes the one-way valve that allows injection of the toxic drug into the syringe in the irreversible manner, and the covering member that covers the first needle such that the first communication channel is open only when the barrel is attached to the barrel attaching part. As a result, the toxic drug is not splashed and leaked, and the aerosol is not exposed outside the system. Moreover, the sealing member prevents leakage of the drug solution from the barrel. Therefore, the drug solution preparing kit is safe because the toxic drug is not exposed in the ambient environment upon preparation of the drug solution, and can be suitably used upon preparation of the drug solution.

The invention claimed is:

1. A drug solution preparing kit comprising a drug solution-filled syringe and a transfusing tool,
   wherein said drug solution-filled syringe includes
   a cylinder-shaped barrel of which a tip end and a base end are open,
   a sealing member which seals said tip end and can not be removed from said tip end, and
   a plunger which is inserted into said barrel in a liquid-tight manner and a slidable manner,
   said barrel, said plunger and said sealing member define a space filled with a drug solution, and
   said transfusing tool includes
   a barrel attaching part to which said barrel can be attached,
   a first needle which is provided on said barrel attaching part and can penetrate through said sealing member,
   a second needle which can penetrate through a plug body of an infusion container, an outlet port which is blocked with a blocking member through which a bottle needle of an infusion line can penetrate,
   a first communication channel which establishes communicative connection between said first needle and said second needle,
   a second communication channel which establishes communicative connection between said second needle and said outlet port and is formed independently of said first communication channel,
   a covering member which covers said first needle such that said first communication channel is open only when said barrel is attached to said barrel attaching part, and
   a one-way valve which is provided on said first communication channel and allows only a fluid flowing from a direction of a tip end of the first needle to pass therethrough in an irreversible manner.

2. The drug solution preparing kit according to claim 1, wherein an opening of said first communication channel, which is formed in said second needle, is farther in position than an opening of said second communication channel.

3. The drug solution preparing kit according to claim 1, wherein said second communication channel is provided with a stopcock.

4. The drug solution preparing kit according to claim 1, wherein said second communication channel is provided with a branched part, and a discharge port, which has a one-way valve allowing only gas from the system to pass therethrough and a hydrophobic filter, is provided so as to be communicatively connected to said branched part.

5. The drug solution preparing kit according to claim 3, wherein said branched part is provided with a stopcock capable of switching between the communicative connection from said second communication channel to said outlet port and the communicative connection from said second communication channel to said discharge port.

6. The drug solution preparing kit according to claim 1, wherein the opening of the first communication channel of said second needle is provided at a side portion of said second needle.

7. The drug solution preparing kit according to claim 1, wherein the coupling between the transfusing tool and the infusion container can not be cancelled once said second needle penetrates through the plug body of the infusion container.

8. The drug solution preparing kit according to claim 1, wherein said barrel attaching part includes a lock means for locking said barrel when said barrel is attached to said barrel attaching part, and the lock can be cancelled upon removal of said barrel from said barrel attaching part.

9. The drug solution preparing kit according to claim 1, wherein said sealing member has a tip end on which an annular hood is formed.

\* \* \* \* \*